US006486153B1

(12) United States Patent
Castro Pineiro et al.

(10) Patent No.: US 6,486,153 B1
(45) Date of Patent: Nov. 26, 2002

(54) PHENYLINDOLE DERIVATIVES AS 5-HT$_{2A}$ RECEPTOR LIGANDS

(75) Inventors: Jose Luis Castro Pineiro, Bishops Stortford (GB); Steven Michael Hutchins, Somerville, NJ (US); Stephen John Lewis, London (GB); Michael Rowley, Chelmsford (GB); Adrian Leonard Smith, Great Dunmow (GB); Graeme Irvine Stevenson, Saffron Walden (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/508,046

(22) PCT Filed: Sep. 1, 1998

(86) PCT No.: PCT/GB98/02616

§ 371 (c)(1),
(2), (4) Date: Mar. 3, 2000

(87) PCT Pub. No.: WO99/11619

PCT Pub. Date: Mar. 11, 1999

(30) Foreign Application Priority Data

Sep. 4, 1997 (GB) .............................................. 9718833

(51) Int. Cl.$^7$ .................... C07D 209/14; C07D 209/16; C07D 401/06; A61K 31/4045; A61K 31/404
(52) U.S. Cl. .............................. 514/217.08; 514/227.8; 514/235.2; 514/253.01; 514/253.06; 514/254.09; 514/278; 514/323; 514/414; 514/415; 540/602; 544/62; 544/143; 544/331; 544/363; 544/364; 544/373; 546/19; 546/201; 548/455; 548/467; 548/506
(58) Field of Search ............................. 540/602; 544/62, 544/143, 381, 363, 364, 373; 546/19, 201; 548/455, 467, 506; 514/217.08, 227.8, 235.2, 253.06, 254.09, 253.01, 252.14, 278, 323, 414, 415

(56) References Cited

U.S. PATENT DOCUMENTS 5,703,070 A  12/1997  Lavielle et al. ............. 514/212

FOREIGN PATENT DOCUMENTS

| EP | 0 747 379 | 12/1996 |
| FR | 1477152 | * 4/1967 |
| FR | A-2102282 | 7/1972 |
| FR | A-2181559 | 7/1973 |
| JP | A 55-151505 | 6/1993 |
| WO | WO 91/18602 | 12/1991 |
| WO | WO97/21435 | 6/1997 |
| WO | WO97/21703 | 6/1997 |

OTHER PUBLICATIONS

Gungor et al., N6–substituted Adenosine Receptor Agonists. J. Med. Chem., 37(25), pp. 4307–4316, 1994.*
Sachez et al. PubMed Abstract, Behav. Pharmacol. 11(3–4): 291–8, Jun. 2000.*
Moore N.A., PubMed Abstract, Br. J. Psychiatry Suppl., (38):5–11, 1999.*
D.C. Dyer. *Life Sciences*, 1993, 53, pp. 223–228.
Ames, et al., *J. chem. Soc.*, 1959, pp. 3388–3399.
Julia, et al., *Annales de l'Institut Pasteur*, 1965, pp. 343–362.
Hiriyakkanavar & Siddappa, *Indian J. Chem.*, 1966, 4, pp. 188–190.
Joshi, et al., *Agric. Biol. Chem.*, 1978, 42, pp. 1723–1726.
Joshi, et al., *Monatsh. Chem.*, 1980, 111, pp. 1343–1350.
Agarwal, et al., J. Indian Chem Soc., 1980, 57, pp. 742–743.

* cited by examiner

*Primary Examiner*—Deepak R. Rao
(74) *Attorney, Agent, or Firm*—James L. McGinnis; Melvin Winokur

(57) ABSTRACT

A class of tryptamine analogues bearing an optionally substituted phenyl nucleus at the 2-position are selective antagonists of the human 5-HT$_{2A}$ receptor and are therefore useful as pharmaceutical agents, especially in the treatment and/or prevention of adverse neurological conditions, including psychotic disorders such as schizophrenia.

14 Claims, No Drawings

PHENYLINDOLE DERIVATIVES AS 5-HT$_{2A}$ RECEPTOR LIGANDS

This application is a 371 of PCT/GB98/02616 filed Sep. 1, 1998.

The present invention relates to the use of a class of indole derivatives which act on serotonin receptors (also known as 5-hydroxytryptamine or 5-HT receptors). More particularly, the invention concerns analogues of tryptamine bearing an optionally substituted phenyl substituent at the 2-position. These compounds are selective antagonists of the human 5-HT$_{2A}$ receptor and are therefore useful as pharmaceutical agents, especially in the treatment and/or prevention of adverse conditions of the central nervous system, including psychotic disorders such as schizophrenia.

Schizophrenia is a disorder which is conventionally treated with drugs known as neuroleptics. In many cases, the symptoms of schizophrenia can be treated successfully with so-called "classical" neuroleptic agents such as haloperidol. Classical neuroleptics generally are antagonists at dopamine D$_2$ receptors.

Notwithstanding their beneficial antipsychotic effects, classical neuroleptic agents such as haloperidol are frequently responsible for eliciting acute extrapyramidal symptoms (movement disorders) and neuroendocrine (hormonal) disturbances. These side-effects, which plainly detract from the clinical desirability of classical neuroleptics, are believed to be attributable to D$_2$ receptor blockade in the striatal region of the brain.

The compound (+)-α-(2,3-dimethoxyphenyl)-1-[2-(4-fluorophenyl)ethyl]-4-piperidinemethanol (also known as MDL-100,907) is described in WO 91/18602. In preclinical studies, MDL-100,907 failed to induce catalepsy and failed to block apomorphine-induced stereotyped behaviour in animal models, strongly suggesting that this compound would be free from any liability to cause extrapyramidal side-effects. MDL-100,907 is currently undergoing clinical trials in schizophrenic patients and has demonstrated efficacy in a multicentre, placebo-controlled study for antipsychotic potential, with no neurological adverse effects. Pharmacologically, MDL-100,907 has been shown to be a potent antagonist of human 5-HT$_{2A}$ receptors, whilst being essentially devoid of activity at the human dopamine D$_2$ receptor. It is accordingly believed that compounds which can interact selectively with the 5-HT$_{2A}$ receptor relative to the dopamine D$_2$ receptor will display the beneficial level of antipsychotic activity associated with 5-HT$_{2A}$ receptor antagonism, whilst minimizing or even avoiding the extrapyramidal and other side-effects arising from an interaction with dopamine D$_2$ receptors.

The compounds of use in the present invention are potent antagonists of the human 5-HT$_{2A}$ receptor, and are accordingly of benefit in the treatment and/or prevention of psychotic disorders such as schizophrenia. The compounds of use in the invention may display more effective binding to the human 5-HT$_{2A}$ receptor than to the human dopamine D$_2$ receptor, and they can therefore be expected to manifest fewer side-effects than compounds which do not discriminate in their binding affinity as between 5-HT$_{2A}$ and D$_2$ receptors.

By virtue of their potent human 5-HT$_{2A}$ receptor antagonist activity, the compounds of use in the present invention are also effective in the treatment of neurological conditions including depression, anxiety, panic disorder, obsessive-compulsive disorder, pain, sleep disorders such as insomnia, eating disorders such as anorexia nervosa, and dependency or acute toxicity associated with narcotic agents such as LSD or MDMA; and cardiovascular conditions including variant angina, Raynaud's phenomenon, intermittent claudication, coronary and peripheral vasospasms, fibromyalgia, cardiac arrhythmias and thrombotic illness. They may also be generally of benefit in the inhibition of platelet aggregation, as well as in controlling the extrapyramidal symptoms associated with the administration of neuroleptic agents. They may further be effective in the lowering of intraocular pressure and may therefore be beneficial in treating glaucoma (cf. T. Mano et al. and H. Takaneka et al., *Investigative Ophthalmology and Visual Science,* 1995, vol. 36, pages 719 and 734 respectively).

Being 5-HT$_{2A}$ receptor antagonists, the compounds of use in the present invention may also be beneficial in preventing or reducing the toxic symptoms associated with the intake of ergovaline in animals consuming *Acremonium coenophialum* infected tall fescue (cf. D. C. Dyer, *Life Sciences,* 1993, 53, 223–228).

The preparation of a series of indole derivatives, including 3-aminoalkyl-2-phenylindoles, for pharmacological study is described in Ames et al., *J. Chem. Soc.,* 1959, 3388–3399. No actual pharmaceutical utility is, however, ascribed to the compounds disclosed therein.

Julia et al. in *Annales de l'Institut Pasteur,* 1965, 343–362, describe the preparation of a number of 2-aryltryptamine derivatives, which are stated to have weak antiserotonin (rat uterus) activity.

Agarwal et al. in *Indian Drugs,* 1979, 209–212, and in *J. Indian Chem. Soc.,* 1980, 57, 742–743, describe the synthesis of inter alia the compound 3-[2-(2-methylpiperidin-1-yl)ethyl]-2-phenyl-1H-indole. However, no pharmacological activity is ascribed in either publication to this specific compound.

In JP-A-55-151505 is described a class of indoles, including 3-aminoalkyl-2-phenylindole derivatives which are optionally substituted on the 2-phenyl moiety and on the benzo moiety of the indole nucleus. These compounds are stated therein to be fungicides.

Hiriyakkanavar & Siddappa in *Indian J. Chem.,* 1966, 4, 188–190, describe the synthesis of various 5,7-dimethyl-substituted 2-phenyltryptamine derivatives, which are stated to exhibit antiserotonin activity.

Joshi et al. in *Agric. Biol. Chem.,* 1978, 42, 1723–1726, and in *Monatsh. Chem.,* 1980:, 111, 1343–1350, describe various fluorinated analogues of 2-phenyltryptamine. Certain of these compounds are stated to act as mild stimulants.

In none of the prior art publications referred to above, in which 2-phenyl analogues of tryptamine are described, is there any disclosure or suggestion that such compounds might be potent and selective antagonists of the human 5-HT$_{2A}$ receptor, nor indeed that they might be of particular benefit in the treatment in particular of neurological conditions, including psychotic disorders such as schizophrenia.

FR-A-2102282 and FR-A-2181559 describe separate series of inter alia 2-phenyltryptamine analogues, both of which are stated to possess a variety of actions on the nervous system.

The compounds of use in the present invention are potent and selective 5-HT$_{2A}$ receptor antagonists having a human 5-HT$_{2A}$ receptor binding affinity ($K_i$) of 100 nM or less, typically of 50 nM or less and preferably of 10 nM or less. The compounds of use in the invention may possess at least a 10-fold selective affinity, suitably at least a 20-fold selective affinity and preferably at least a 50-fold selective affinity, for the human 5-HT$_{2A}$ receptor relative to the human dopamine D$_2$ receptor.

The present invention provides the use of a compound of formula I, or a pharmaceutically acceptable salt thereof:

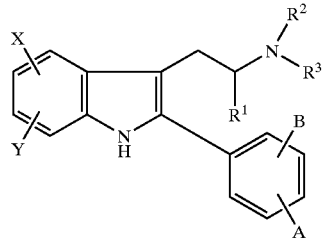
(I)

wherein

A and B independently represent hydrogen, halogen, cyano, nitro, trifluoromethyl, trifluoromethoxy, $C_{1-6}$ alkyl or $C_{1-6}$ alkoxy;

X and Y independently represent hydrogen, halogen, $C_{1-6}$ alkyl, $C_{1-6}$ alkoxy or phenyl;

$R^1$ represents hydrogen or $C_{1-6}$ alkyl;

$R^2$ represents hydrogen, methyl, ethyl, 2-methoxyethyl, n-propyl, isopropyl, n-butyl, 2-methylpropyl, tert-butyl or n-pentyl; and $R^3$ represents $C_{1-6}$ alkyl, $C_{2-6}$ alkenyl, $C_{3-9}$ cycloalkyl, aryl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^2$ and $R^3$ taken together with the intervening nitrogen atom represent a group of formula (a), (b), (c), (d), (e), (f), (g), (h), (i), (j), (k), (l) or (m):

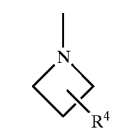
(a)

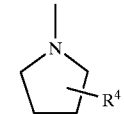
(b)

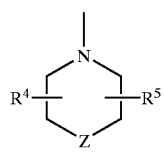
(c)

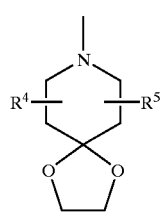
(d)

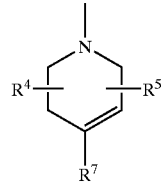
(e)

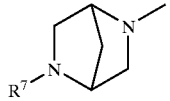
(f)

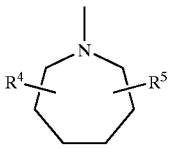
(g)

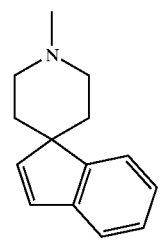
(h)

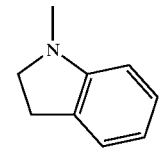
(i)

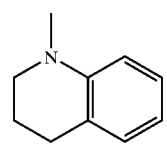
(j)

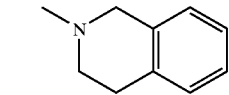
(k)

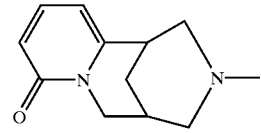
(l)

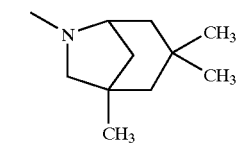
(m)

in which the broken line represents an optional chemical bond;

Z represents oxygen, sulphur, N—$R^6$ or $CR^7R^8$;

$R^4$ represents hydrogen, $C_{1-6}$ alkyl, $C_{1-6}$ alkoxy($C_{1-6}$) alkyl, $C_{3-7}$ heterocycloalkyl($C_{1-6}$)alkyl or aryloxy;

$R^5$ represents hydrogen, $C_{1-6}$ alkyl or $C_{1-6}$ alkoxy($C_{1-6}$) alkyl;

$R^6$ represents hydrogen, —$COR^9$ or —$CO_2R^9$; or $C_{1-6}$ alkyl, $C_{2-6}$ alkenyl, $C_{3-9}$ cycloalkyl, aryl($C_{1-6}$)alkyl, aryl($C_{2-6}$)alkenyl, $C_{3-7}$ heterocycloalkyl($C_{1-6}$)alkyl or heteroaryl, any of which groups may be optionally substituted by one or more substituents;

$R^7$ represents hydrogen, hydrocarbon, a heterocyclic group, —$COR^9$ or —$CO_2R^9$;

$R^8$ represents hydrogen, phenyl or acetoxy; and $R^9$ represents $C_{1-6}$ alkyl;

for the manufacture of a medicament for the treatment and/or prevention of clinical conditions for which a selective antagonist of 5-$HT_{2A}$ receptors is indicated, especially psychotic disorders including schizophrenia.

The present invention also provides a method for the treatment and/or prevention of clinical conditions for which a selective antagonist of 5-$HT_{2A}$ receptors is indicated, especially psychotic disorders including schizophrenia, which comprises administering to a patient in need of such treatment an effective amount of a compound of formula I as defined above or a pharmaceutically acceptable salt thereof.

A particular subset of compounds of use in the present invention comprises the compounds of formula I as depicted above, and pharmaceutically acceptable salts thereof, wherein A, B, X, Y and $R^1$ are as defined above;

$R^2$ represents hydrogen, methyl or ethyl; and $R^3$ represents $C_{1-6}$ alkyl, $C_{3-9}$ cycloalkyl, aryl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^2$ and $R^3$ taken together with the intervening nitrogen atom represent a group of formula (a) to (k) as defined above, in which $R^4$ represents hydrogen or $C_{1-6}$ alkyl; and Z, $R^5$, $R^6$, $R^7$, $R^8$ and $R^9$ are as defined above.

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of use in the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-9}$ cycloalkyl, $C_{3-9}$ cycloalkyl($C_{1-6}$)alkyl, indanyl, aryl, aryl ($C_{1-6}$)alkyl and aryl($C_{2-6}$)alkenyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, n-butyl, isobutyl, tert-butyl, n-pentyl and 2,2-dimethylpropyl.

Suitable alkenyl groups include straight-chained and branched alkenyl groups containing from 2 to 6 carbon atoms. Typical examples include vinyl, allyl, 2-methylpropenyl and dimethylallyl groups.

Suitable alkynyl groups include straight-chained and branched alkynyl groups containing from 2 to 2 carbon atoms. Typical examples include ethynyl and propargyl groups.

Suitable cycloalkyl groups include groups containing from 3 to 9 carbon atoms. Particular cycloalkyl groups are cyclopropyl, cyclopentyl, cyclohexyl and cyclooctyl.

Typical examples of $C_{3-9}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl.

Particular aryl($C_{1-6}$)alkyl groups include benzyl, phenylethyl, phenylpropyl, phenylbutyl and naphthylmethyl.

Typical aryl($C_{2-6}$)alkenyl groups include phenylethenyl and phenylpropenyl.

Suitable heterocycloalkyl groups include tetrahydrofuryl, tetrahydrothienyl, azetidinyl, pyrrolidinyl, piperidinyl, piperazinyl and morpholinyl groups.

Typical $C_{3-7}$ heterocycloalkyl($C_{1-6}$)alkyl groups include tetrahydrofurylmethyl, morpholinylethyl and pyrrolidinylpropyl.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, benzimidazolonyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups, as well as the substituents $R^3$ and $R^6$, may in turn be optionally substituted by one or more groups, preferably by one or two optional groups, selected from $C_{1-6}$ alkyl, adamantyl, phenyl or halophenyl (except when $R^3$ is $C_{1-3}$ alkyl), benzyl, thiadiazolyl, halogen, $C_{1-6}$ haloalkyl, $C_{1-6}$ aminoalkyl, difluoromethyl, trifluoromethyl, hydroxy, $C_{1-6}$ alkoxy, difluoromethoxy, trifluoromethoxy, aryloxy, benzyloxy, OXO, $C_{1-3}$ alkylenedioxy, 1,3-dioxabutylene, nitro, cyano, carboxy, $C_{2-6}$ alkoxycarbonyl, $C_{2-6}$ alkoxycarbonyl($C_{1-6}$) alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $-NR^vR^w$, $-NR^vCOR^w$, $-NR^vCO_2R^w$, $-NR^vSO_2R^w$, $-CH_2NR^vSO_2R^w$, $-NHCONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl, or $R^v$ and $R^w$ together represent a $C_{2-6}$ alkylene group.

When $R^v$ and $R^w$ together represent a $C_{2-6}$ alkylene group, this group may be an ethylene, propylene, butylene, pentamethylene or hexamethylene group, preferably butylene or pentamethylene.

The term "halogen" as used herein includes fluorine, chlorine, bromine and iodine, especially fluorine or chlorine.

Where the compounds of use in the invention have at least one asymmetric centre, they may accordingly exist as enantiomers. Where the compounds of use in the invention possess two or more asymmetric centres, they may additionally exist as diastereoisomers. It is to be understood that the use of all such isomers and mixtures thereof in any proportion is encompassed within the scope of the present invention.

Particular values for the substituent A in the compounds of formula I above include hydrogen, fluoro, trifluoromethyl and methyl, especially hydrogen.

Suitably, B represents hydrogen, fluoro, chloro, cyano, nitro, trifluoromethyl, trifluoromethoxy, methyl or methoxy.

Particular values for the substituent X include hydrogen and fluoro, especially hydrogen.

Suitably, Y represents hydrogen, fluoro, chloro, bromo, methyl, methoxy or phenyl.

Suitably, $R^1$ represents hydrogen or methyl, especially hydrogen.

Suitably, $R^2$ represents hydrogen, methyl or ethyl, typically hydrogen or methyl.

In one embodiment, $R^2$ represents hydrogen. In another embodiment, $R^2$ is methyl.

Illustrative values of $R^3$ include methyl, ethyl, n-propyl, isopropyl, n-butyl, 2-methylpropyl, tert-butyl, n-pentyl, 2-methylpropenyl, cyclopropyl, cyclobutyl, cyclopentyl, cyclohexyl, cyclooctyl, phenyl, tetrahydrothienyl, piperidinyl, tetrahydrofurylmethyl, morpholinylethyl, pyrrolidinylpropyl, morpholinylpropyl and furylmethyl, any of which groups may be optionally substituted by one or more substituents.

Representative values of $R^3$ include methyl, ethyl, n-propyl, isopropyl, cyclopropyl, cyclopentyl, cyclooctyl, phenyl, tetrahydrothienyl, piperidinyl, tetrahydrofurylmethyl, morpholinylethyl, pyrrolidinylpropyl and furylmethyl, any of which groups may be optionally substituted by one or more substituents.

The moiety $R^3$ may be unsubstituted, or substituted by one or more substituents. Preferably, $R^3$ is unsubstituted, or substituted by one or two substituents. Examples of typical substituents on the moiety $R^3$ include benzyl, fluoro, chloro, bromo, trifluoromethyl, methoxy, ethoxy, isopropoxy, difluoromethoxy, trifluoromethoxy, oxo, 1,3-dioxabutylene and diisopropylamino.

Specific values of $R^3$ include methyl, ethyl, fluoroethyl, trifluoroethyl, methoxyethyl, diisopropylamino-ethyl, n-propyl, fluoropropyl, isopropyl, n-butyl, 2-methylpropyl, tert-butyl, n-pentyl, 2-methylpropenyl, cyclopropyl, cyclobutyl, cyclopentyl, cyclohexyl, cyclooctyl, phenyl, fluorophenyl, chlorophenyl, dichlorophenyl, methoxyphenyl, dimethoxyphenyl, trimethoxyphenyl, ethoxyphenyl, isopropoxyphenyl, difluoromethoxy-phenyl, trifluoromethoxy-phenyl, 1,3-dioxabutylenephenyl, tetrahydrothienyl dioxide, benzyl-piperidinyl, tetrahydrofurylmethyl, morpholinethyl, pyrrolidinylpropyl, morpholinylpropyl and furylmethyl.

Particular values of $R^3$ include methyl, ethyl, diisopropylaminoethyl, n-propyl, isopropyl, cyclopropyl, cyclopentyl, cyclooctyl, phenyl, fluorophenyl, chlorophenyl, dichlorophenyl, methoxyphenyl, dimethoxyphenyl, trimethoxyphenyl, ethoxyphenyl, isopropoxyphenyl, difluoromethoxy-phenyl, trifluoromethoxy-phenyl, 1,3-dioxabutylenephenyl, tetrahydrothienyl dioxide, benzyl-piperidinyl, tetrahydrofurylmethyl, morpholinylethyl, pyrrolidinylpropyl and furylmethyl.

In one embodiment, Z represents oxygen or sulphur. In another embodiment, Z represents $CR^7R^8$.

In a further embodiment, Z represents oxygen, sulphur or $N-R^6$. In a still further embodiment, Z represents $N-R^6$ or $CR^7R^8$. In a yet further embodiment, Z represents oxygen, sulphur or $CR^7R^8$.

Suitably, $R^4$ represents hydrogen, methyl, methoxymethyl, pyrrolidinylmethyl or phenoxy, especially hydrogen or methoxymethyl, and more especially hydrogen. More particularly, $R^4$ may represent hydrogen or methyl, especially hydrogen.

Suitably, $R^5$ represents hydrogen, methyl, ethyl, n-propyl or methoxymethyl, especially hydrogen.

Illustrative values of $R^6$ include hydrogen, acetyl and tert-butoxycarbonyl; and methyl, ethyl, n-propyl, isopropyl, allyl, cyclopentyl, cyclohexyl, benzyl, phenylethyl, phenylethenyl, morpholinylethyl, pyridinyl, quinolinyl, isoquinolinyl, pyrimidinyl and benzofuryl, any of which groups may be optionally substituted by one or more substituents.

Representative values of $R^6$ include hydrogen, acetyl and tert-butoxycarbonyl; and methyl, ethyl, propyl, allyl, cyclohexyl, benzyl, phenylethyl, phenylethenyl, morpholinylethyl, pyridinyl, quinolinyl, isoquinolinyl, pyrimidinyl and benzofuryl, any of which groups may be optionally substituted by one or more substituents.

The moiety $R^6$ may be unsubstituted, or substituted by one or more substituents. Preferably, $R^6$ is unsubstituted, or substituted by one or two substituents. Examples of typical substituents on the moiety $R^6$ include methyl, ethyl, tert-butyl, phenyl, fluorophenyl, chlorophenyl, fluoro, chloro, trifluoromethyl, methoxy, ethoxy, benzyloxy, methylenedioxy, nitro, cyano, acetoxy, methylthio, dimethylamino, diethylamino, dipropylamino, N-methyl-N-phenylaminocarbonyl and pyrrolidinylcarbonyl. More specific examples of typical substituents on the moiety $R^6$ include methyl, ethyl, tert-butyl, phenyl, fluorophenyl, chlorophenyl, fluoro, chloro, trifluoromethyl, methoxy, ethoxy, benzyloxy, methylenedioxy, nitro, cyano, acetoxy, methylthio, dimethylamino, diethylamino, N-methyl-N-phenylaminocarbonyl and pyrrolidinylcarbonyl.

Specific values for the moiety $R^6$ include hydrogen, acetyl, tert-butoxycarbonyl, methyl, benzyloxymethyl, N-methyl-N-phenylaminocarbonyl-methyl, pyrrolidinylcarbonyl-methyl, ethyl, methoxyethyl, acetoxyethyl, dimethylamino-ethyl, diethylamino-ethyl, dipropylamino-ethyl, dimethylamino-propyl, isopropyl, allyl, cyclopentyl, cyclohexyl, benzyl, tert-butylbenzyl, diphenylmethyl, (chlorophenyl)(phenyl)methyl, di(fluorophenyl)methyl, di(chlorophenyl)methyl, chlorobenzyl, methylenedioxy-benzyl, 1-phenylethyl, 2-phenylethyl, chlorophenyl-ethenyl, cyanophenyl-ethenyl, morpholinylethyl, pyridinyl, trifluoromethyl-pyridinyl, (chloro)(trifluoromethyl)pyridinyl, trifluoromethyl-quinolinyl, isoquinolinyl, pyrimidinyl, trifluoromethyl-pyridimidinyl and benzofuryl.

Particular values of $R^6$ include hydrogen, acetyl, tert-butoxycarbonyl, methyl, benzyloxymethyl, N-methyl-N-phenylaminocarbonyl-methyl, pyrrolidinylcarbonyl-methyl, ethyl, methoxyethyl, acetoxyethyl, diethylamino-ethyl, dimethylamino-propyl, allyl, cyclohexyl, benzyl, tert-butylbenzyl, diphenylmethyl, (chlorophenyl)(phenyl)methyl, di(fluorophenyl)methyl, di(chlorophenyl)methyl, chlorobenzyl, methylenedioxy-benzyl, phenylethyl, chlorophenyl-ethenyl, cyanophenyl-ethenyl, morpholinylethyl, pyridinyl, trifluoromethyl-pyridinyl, (chloro)(trifluoromethyl)pyridinyl, trifluoromethyl-quinolinyl, isoquinolinyl, pyrimidinyl, trifluoromethyl-pyridimidinyl and benzofuryl.

Suitable values of $R^7$ include hydrogen, $C_{2-6}$ alkylcarbonyl and $C_{2-6}$ alkoxycarbonyl; and $C_{1-6}$ alkyl, $C_{2-6}$ alkenyl, $C_{3-7}$ cycloalkyl, aryl, aryl($C_{1-6}$)alkyl1, aryl($C_{2-6}$)alkenyl, $C_{3-7}$ heterocycloalkyl($C_{1-6}$)alkyl and heteroaryl, any of which groups may be optionally substituted by one or more substituents.

Representative values of $R^7$ include hydrogen, acetyl and tert-butoxycarbonyl; and methyl, ethyl, propyl, allyl, cyclohexyl, phenyl, benzyl, phenylethyl, phenylpropyl, phenylbutyl, phenylethenyl, phenylpropenyl, morpholinylethyl, pyridinyl, quinolinyl, isoquinolinyl, pyrimidinyl, benzofuryl and benzimidazolonyl, any of which groups may be optionally substituted by one or more substituents.

The moiety $R^7$ may be unsubstituted, or substituted by one or more substituents. Preferably, $R^7$ is unsubstituted, or substituted by one or two substituents. Examples of typical substituents on the moiety $R^7$ include methyl, ethyl, tert-butyl, phenyl, fluorophenyl, chlorophenyl, fluoro, chloro, trifluoromethyl, methoxy, ethoxy, benzyloxy, methylenedioxy, nitro, cyano, acetoxy, methylthio, dimethylamino, diethylamino, N-methyl-N-phenylaminocarbonyl and pyrrolidinylcarbonyl.

Specific values for the moiety $R^7$ include hydrogen, acetyl, tert-butoxycarbonyl, methyl, benzyloxymethyl, N-methyl-N-phenylaminocarbonyl-methyl, pyrrolidinylcarbonyl-methyl, ethyl, methoxyethyl, acetoxyethyl, diethylamino-ethyl, dimethylamino-propyl, allyl, cyclohexyl, phenyl, methylphenyl, dimethylphenyl, ethylphenyl, fluorophenyl, chlorophenyl, dichlorophenyl, trifluoromethyl-phenyl, (chloro)(trifluoromethyl)phenyl, bis(trifluoromethyl)phenyl, methoxyphenyl, (dichloro)(methoxy)phenyl, dimethoxyphenyl, trimethoxyphenyl, ethoxyphenyl, methylenedioxy-phenyl, nitrophenyl, (dinitro)(trifluoromethyl)phenyl, cyanophenyl, dicyanophenyl, methylthiophenyl, benzyl, tert-butylbenzyl, diphenylmethyl, (chlorophenyl)(phenyl)methyl, di(fluorophenyl)methyl, di(chlorophenyl)methyl, chlorobenzyl, methylenedioxy-benzyl, phenylethyl, 3,3-diphenylpropyl, 4-phenylbut-2-yl, chlorophenyl-ethenyl, cyanophenyl-ethenyl, phenylpropenyl, morpholinylethyl, pyridinyl, trifluoromethyl-pyridinyl, (chloro)(trifluoromethyl)pyridinyl, trifluoromethyl-quinolinyl, isoquinolinyl, pyrimidinyl, trifluoromethyl-pyridimidinyl, benzofuryl and benzimidazolonyl.

In relation to formula (c) above in which Z represents $CR^7R^8$, the moiety $R^7$ suitably represents hydrogen, methyl, benzyloxymethyl, phenyl, methoxyphenyl, benzyl, phenylethyl or benzimidazolonyl. More particularly, $R^7$ in this context may suitably represent hydrogen, benzyloxymethyl, benzyl, phenylethyl or benzimidazolonyl.

In relation to formula (e) above, the moiety $R^7$ suitably represents methylenedioxy-phenyl, chlorophenyl-ethenyl, cyanophenyl-ethenyl or benzofuryl.

In relation to formula (f) above, the moiety $R^7$ suitably represents benzyl.

Suitably, $R^8$ represents hydrogen.

Suitably, $R^9$ represents methyl or tert-butyl.

Specific compounds of use in the present invention include:
3-[2-(N,N-dimethylamino)ethyl]-2-phenyl-1H-indole;
3-[2-(N,N-diethylamino)ethyl]-2-phenyl-1H-indole;
2-phenyl-3-[2-(pyrrolidin-1-yl)ethyl]-1H-indole;
2-phenyl-3-[2-(piperidin-1-yl)ethyl]-1H-indole;
3-[2-(2-methylpiperidin-1-yl)ethyl]-2-phenyl-1H-indole;
3-[2-homopiperidin-1-yl)ethyl]-2-phenyl-1H-indole;
3-[2-(morpholin-4-yl)ethyl]-2-phenyl-1H-indole ;
2-(4-fluorophenyl)-3-[2-(piperidin-1-yl)ethyl]-1H-indole;
and pharmaceutically acceptable salts thereof.

Certain compounds falling within the definition of formula I above are novel. Accordingly, in a further aspect, the present invention provides a compound of formula I as defined above, or a salt thereof, wherein B represents trifluoromethyl or trifluoromethoxy.

In another aspect, the present invention provides a compound of formula I as defined above, or a salt thereof, wherein Y represents phenyl.

In another aspect, the present invention provides a compound of formula I as defined above, or a salt thereof, provided that:

(i) when A and B independently represent hydrogen, halogen, cyano, nitro, alkyl or alkoxy, and X and Y independently represent hydrogen, halogen, alkyl or alkoxy, then either $R^3$ does not represent alkyl, or $R^2$ and $R^3$ taken together with the intervening nitrogen atom do not represent piperidin-1-yl or morpholin-4-yl; and (ii) when A, B, X, Y and $R^1$ each represents hydrogen, then $R^2$ and $R^3$ taken together with the intervening nitrogen atom do not represent pyrrolidin-1-yl, 2-methylpiperidin-1-yl or homopiperidin-1-yl.

Particular sub-classes of novel compounds in accordance with the present invention are represented by the compounds of formula IA and IB, and salts thereof:

(IA)

(IB)

wherein $R^2$ and $R^3$ are as defined above.

Specific compounds in accordance with the present invention include those compounds disclosed in the accompanying Examples, with the exception of Example Nos. 1, 9, 22, 34, 36, 38, 49 and 55.

The invention also provides pharmaceutical compositions comprising one or more of the novel compounds according to the invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

If desired, the compounds of use in this invention may be co-administered with another anti-schizophrenic medicament, for example one producing its effects via dopamine $D_2$ and/or $D_4$ receptor subtype blockade. In such circumstances, an enhanced anti-schizophrenic effect may be envisaged without a corresponding increase in side-effects such as those caused by, for example, $D_2$ receptor subtype blockade; or a comparable anti-schizophrenic effect with reduced side-effects may alternatively be envisaged. Such co-administration may be desirable where a patient is already established on an anti-schizophrenic treatment regime involving conventional anti-schizophrenic medicaments. Suitable anti-schizophrenic medicaments of use in combination with the compounds according to the present invention include haloperidol, chlorpromazine, mesoridazine, thioridazine, acetophenazine, fluphenazine, perphenazine, trifluoperazine, chloroprothixene, thiothixene, clozapine, olanzapine, pimozide, molindone, loxapine, sulpiride, risperidone, xanomeline, fananserin and ziprasidone, and pharmaceutically acceptable salts thereof.

The compounds of formula I above, including the novel compounds according to the present invention, may be prepared by a process which comprises reacting a compound of formula II with a compound of formula III:

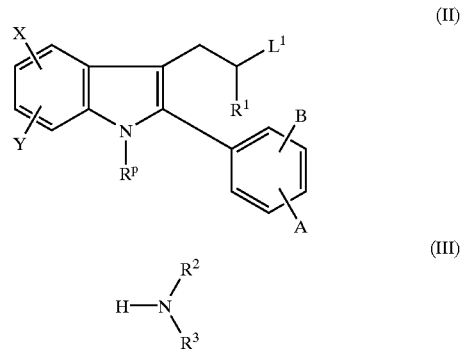

wherein A, B, X, Y, $R^1$, $R^2$ and $R^3$ are as defined above, $L^1$ represents a suitable leaving group and $R^P$ represents a hydrogen atom, an amino-protecting group or an attached resin moiety; followed, where necessary, by removal of the amino-protecting group or attached resin moiety $R^P$.

The leaving group $L^1$ is suitably an alkylsulphonyloxy or arylsulphonyloxy moiety such as trifluoromethanesulphonyloxy (triflyloxy) or p-toluenesulphonyloxy (tosyloxy), preferably triflyloxy.

Where $R^P$ represents an amino-protecting group, this is suitably a carbamoyl moiety, e.g. tert-butoxycarbonyl (BOC), which can readily be removed as required by treatment with acid, typically trifluoroacetic acid, or with base, e.g. sodium methoxide in methanol.

Where $R^P$ represents an attached resin moiety, this is suitably a polymeric moiety such as the commercially available WANG resin, whereby the substituent $R^P$ represents (4-benzyloxycarbonyl) phenoxymethylcopoly(styrene-1% divinylbenzene). The WANG resin can be conveniently removed at the appropriate stage by treatment with pyrrolidine at an elevated temperature, typically in a solvent such as N,N-dimethylformamide.

The reaction between compounds II and III is conveniently effected by stirring in an appropriate solvent, e.g. dichloromethane, 1,2-dichloroethane or N,N-dimethylformamide, optionally under basic conditions, for example in the presence of potassium carbonate.

In an alternative procedure, the compounds of formula I above, including the novel compounds according to the invention, may be prepared by a process which comprises reacting a compound of formula IV with a compound of formula V:

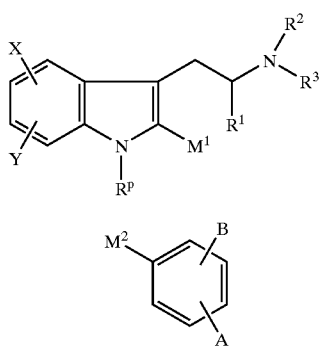

(IV)

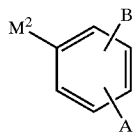

(V)

wherein A, B, X, Y, $R^1$, $R^2$, $R^3$ and $R^p$ are as defined above; one of $M^1$ and $M^2$ represents a suitable leaving group, and the other represents a boronic acid moiety —$B(OH)_2$ or a $_{1-4}$ alkyl ester or anhydride thereof; in the presence of a transition metal catalyst; followed, where necessary, by removal of the amino-protecting group or attached resin moiety $R^p$.

The leaving group $M^1$ or $M^2$ is suitably a halogen atom, e.g. bromine.

The transition metal catalyst of use in the reaction between compounds IV and V is suitably tetrakis (triphenylphosphine)palladium (0);. The reaction is conveniently carried out in an inert solvent such as ethanolic toluene, aqueous tetrahydrofuran or aqueous 1,2-dimethoxyethane, advantageously in the presence of a base such as sodium acetate or sodium carbonate, optionally in the presence of lithium chloride, and typically at an elevated temperature.

Where $L^1$ represents triflyloxy or tosyloxy, the intermediates of formula II above may be prepared by triflylation or tosylation of the corresponding 3-(2-hydroxyethyl)indole derivative using standard techniques, e.g. by treatment with triflic anhydride ($Tf_2O$), typically in a solvent such as dichloromethane or 1,2-dichloroethane and optionally in the presence of a base such as 2,6-di-tert-butyl-4-methylpyridine. The hydroxy compound may in turn be prepared by reaction of a compound of formula V as defined above with a compound of formula VI:

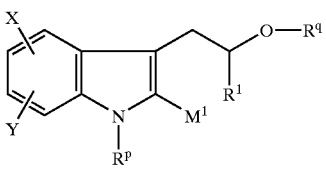

(VI)

wherein X, Y, $R^1$, $R^p$ and $M^1$ are as defined above, and $R^q$ represents hydrogen or a hydroxy-protecting group; under conditions analogous to those defined above for the reaction between compounds IV and V; followed, where necessary, by removal of the hydroxy-protecting group $R^q$.

Where $R^q$ represents a hydroxy-protecting group, this is ideally a tetrahydro-2H-pyran-2-yl moiety, which can conveniently be removed as necessary under acidic conditions, for example by treatment with pyridinium p-toluenesulphonate (PPTS) in a suitable solvent, e.g. ethanol or a mixture of ethanol and 1,2-dichloroethane.

The intermediates of formula IV may be prepared by reacting a compound of formula III as defined above with a compound of formula VII:

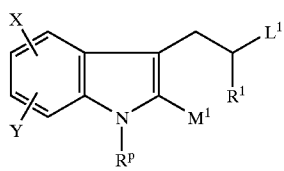

(VII)

wherein X, Y, $R^1$, $R^p$, $L^1$ and $M^1$ are as defined above; under conditions analogous to those described above for the reaction between compounds II and III.

Where $L^1$ represents triflyloxy or tosyloxy, the intermediates of formula VII may be prepared by triflylation or tosylation of the appropriate compound of formula VI wherein $R^q$ represents hydrogen, using standard techniques.

In another procedure, the compounds of formula I above, including the novel compounds according to the invention, may be prepared by a process which comprises reacting a compound of formula III as defined above with a compound of formula VIII:

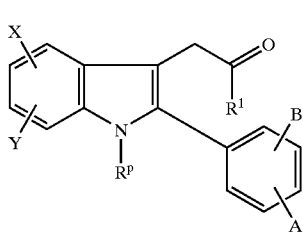

(VIII)

wherein A, B, X, Y, $R^1$ and $R^p$ are as defined above; in the presence of a reducing agent; followed, where necessary, by removal of the amino-protecting group or attached resin moiety $R^p$.

A suitable reducing agent for use in the reaction between compounds III and VIII is sodium triacetoxyborohydride. The reaction is conveniently effected in the presence of acetic acid, typically in an inert solvent such as 1,2-dichloroethane.

In a further procedure, the compounds of formula I above, including the novel compounds according to the invention, may be prepared by a process which comprises reacting a compound of formula IX or an acid addition salt thereof, typically the hydrochloride salt, with a compound of formula X:

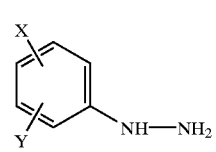

(IX)

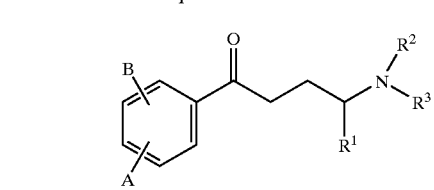

(X)

wherein A, B, X, Y, $R^1$, $R^2$ and $R^3$ are as defined above.

The reaction between compounds IX and X, which is an example of the well-known Fischer indole synthesis, is suitably effected by stirring in ethanol at 25° C., followed by heating in trifluoroacetic acid at 70° C.

In a still further procedure, the compounds of formula I above, including the novel compounds according to the invention, may be prepared by a process which comprises reacting a compound of formula XI with a compound of formula XII (cf Larock and Yum, *J. Am. Chem. Soc.*, 1991, 113, 6689):

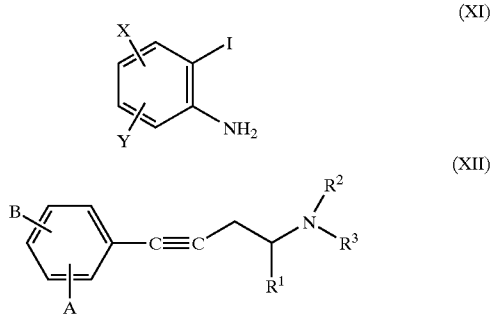

wherein A, B, X, Y, $R^1$, $R^2$ and $R^3$ are as defined above; in the presence of a transition metal catalyst.

Similarly, the intermediates of formula II, or their hydroxy precursors, and the intermediates of formula VIII may be prepared by reacting a compound of formula XI as defined above with the appropriate compound of formula XIII or XIV:

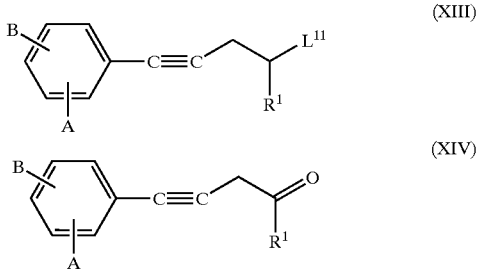

wherein A, B and $R^1$ are as defined above, and $L^{11}$ corresponds to the moiety $L^1$ or represents hydroxy; in the presence of a transition metal catalyst.

The transition metal catalyst employed in the reaction between compound XI and compound XII, XIII or XIV is suitably a palladium-containing catalyst. Typical catalysts include palladium(II) acetate, optionally in the presence of triphenylphosphine, and dichlorobis(triphenylphosphine) palladium(II). A preferred catalyst is dichlorobis (triphenylphosphine)palladium(II).

The transition metal catalysed indole formation reaction between compound XI and compound XII, XIII or XIV is advantageously carried out under basic conditions. Typical basic reagents of use in the reaction include sodium carbonate, potassium carbonate, sodium acetate or potassium acetate, optionally in the presence of lithium chloride or tetra-n-butylammonium chloride; and tetramethylguanidine. A preferred base is tetramethylguanidine. The reaction is conveniently effected in a polar aprotic organic solvent such as N,N-dimethylformamide, typically at an elevated temperature, e.g. a temperature in the region of 80–110° C.

Where they are not commercially available, the starting materials of formula III, V, VI, IX, X, XI, XII, XIII and XIV may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds of use in the invention.

The compounds useful in this invention potently inhibit [$^3$H]-ketanserin binding to the human 5-HT$_{2A}$ receptor expressed in clonal cell lines. Moreover, those compounds of use in the invention which have been tested display a selective affinity for the 5-HT$_{2A}$ receptor relative to the dopamine D$_2$ receptor.

The compounds of the accompanying Examples were all found to possess a K$_i$ value for displacement of [$^3$H]-ketanserin from the human 5-HT$_{2A}$ receptor, when expressed in Chinese hamster ovary (CHO) clonal cell lines, of 100 nM or less.

EXAMPLES 1 TO 107

Method A: 2-Phenyl-3-[2-(piperidin-1-yl)ethyl]-1H-indole (Example 1)

(a) 1-tert-Butoxycarbonyl-3-[2-(tetrahydro-2H-pyran-2-yloxy)ethyl]-1H-indole

4-Dimethylaminopyridine (409 mg) was added to a stirred solution of 3-[2-(tetrahydro-2H-pyran-2-yloxy)ethyl]-1H-indole (T. Fukuyama, *J. Am. Chem. Soc.*, 1994, 116, 3127; 8.22 g) and di-tert-butyl dicarbonate (7.37 g) in dry DCM at room temperature. The resulting solution was stirred at room temperature for 2 h at which time it was diluted with DCM (200 ml) and washed with citric acid (10% aq; 100 ml). The organic layer was separated and dried over MgSO$_4$, filtered and the solvent removed under reduced pressure to give a yellow oil (12.83 g); $^1$H (250 MHz, CDCl$_3$) δ1.60–2.00 (6H, br m), 1.66 (9H, s), 2.99 (2H, t, J=7.5 Hz), 3.47 (1H, m), 3.75 (1H, m), 3.85 (1H, m), 4.00 (1H, m), 4.95 (1H, t, J=2.5 Hz), 7.20 (1H, t, J=7.5 Hz), 7.33 (1H, t, J=7.5 Hz), 7.44 (1H, s), 7.57 (1H, d, J=5.0 Hz) and 8.12 (1H, br d, J=5.0 Hz).

(b) 1-tert-Butoxycarbonyl-2-bromo-3-[2-(tetrahydro-2H-pyran-2-yloxy)ethyl]-1H-indole tert-Butyllithium (28.1 ml of a 1.7 mol solution in pentane) was added slowly to a stirred solution of 1-tert-butoxycarbonyl-3-[2-(tetrahydro-2H-pyran-2-yloxy)ethyl]-

1H-indole (15.0 g) in dry ether at −78° C. under a dry nitrogen atmosphere. During the addition the temperature was maintained below −65° C. The reaction was stirred at −78° C. for 45 min at which time 1,2-dibromotetrafluoroethane (6.24 ml) was added. The reaction mixture was then allowed to warm to room temperature over 18 h, after which time it was quenched with water (100 ml) and extracted into ether (250 ml). The organic layer was separated, washed with water (250 ml) and brine (250 ml), dried over $MgSO_4$, filtered and the solvent removed under reduced pressure to give an orange oil. Purification by flash chromatography ($SiO_2$; n-hexane/ethyl acetate 10:1) afforded the product as a pale yellow oil (7.12 g); $^1H$ (250 MHz, $CDCl_3$) δ1.50–2.00 (6H, br m), 1.61 (9H, s), 3.05 (2H, t, J=7.5 Hz), 3.43 (1H, m), 3.56 (1H, m), 3.74 (1H, m), 3.91 (1H, m), 4.61 (1H, t, J=2.5 Hz), 7.26 (2H, m), 7.54 (1H, d, J=5.0 Hz) and 8.07 (1H, d, J=5.0 Hz).

(c) 2-Bromo-3-[2-(tetrahydro-2H-pyran-2-yloxy)ethyl]-1H-indole 1-tert-Butoxycarbonyl-2-bromo-3-[2-(tetrahydro-2H-pyran-2-yloxy)ethyl]-1H-indole (7.12 g) was added to a 1 mol solution of sodium methoxide in methanol (200 ml) and the resulting mixture warmed to 60° C. for 2 h. After cooling the solvent was removed under reduced pressure and the residue purified immediately by flash chromatography ($SiO_2$; n-hexane/ethyl acetate 10:1) to give the product as a pale yellow oil (4.79 g); 1H (250 MHz, $CDCl_3$) δ1.60–2.00 (6H, br m), 3.03 (2H, t, J=7.5 Hz), 3.42 (1H, m), 3.67 (1H, m), 3.78 (1H, m), 3.83 (1H, m), 4.63 (1H, t, J=2.5 Hz), 7.09 (2H, m), 7.25 (1H, d, J=5.0 Hz), 7.58 (1H, d, J=5.0 Hz) and 8.09 (1H, br s).

(d) Coupling of 2-bromo-3-[2-(tetrahydro-2H-pyran-2-yloxy)ethyl]-1H-indole to 4-nitronphenylcarbonate WANG resin 2-Bromo-3-[2-(tetrahydro-2H-pyran-2-yloxy)ethyl]-1H-indole (3.50 g) and commerically available 4-nitrophenylcarbonate WANG resin (10.80 g, 1.0 mmol/g) were combined together in dry toluene (25 ml) and the solvent removed under reduced pressure. This procedure was repeated twice. The recovered dry mixture was suspended in dry toluene (75 ml) and cooled to −78° C. under a dry nitrogen atmosphere. Potassium bis(trimethylsilyl)-amide (21.6 ml of a 0.5 mol solution in toluene) was then added. The solution was allowed to stir at −78° C. for 10 min and then allowed to warm to room temperature over 1 h. The resin was then filtered off and washed with DMF (4×250 ml), DCM (4×250 ml), MeOH (4×250 ml) and ether (250 ml) to give 1-[4-benzyloxycarbamoyl]phenoxymethyl-copoly(styrene-1%-divinylbenzene)-2-bromo-3-[2-(tetrahydro-2H-pyran-2-yloxy)ethyl]-1H-indole. The recovered resin was then re-suspended in dry DCM (100 ml) and capped by treatment with excess dimethylamine (2×20 ml; 1.0 mol solution in THF), then dried under high vacuum overnight. The resin was once again filtered and the wash procedure repeated using DMF (4×250 ml), DCM (4×250 ml), MeOH (4×250 ml) and ether (250 ml). A portion of the recovered resin (100 mg) was then suspended in dry DMF (3.0 ml) containing 5% pyrrolidine and heated to 110° C. for 4 h. The resin was filtered off and the solvent removed from the filtrate under reduced pressure to afford the recovered starting material giving a loading of 0.62 mmol/g; $^1H$ (250 MHz, $CDCl_3$) δ1.60–2.00 (6H, br m), 3.03 (2H, t, J=7.5 Hz), 3.42 (1H, m), 3.67 (1H, m), 3.78 (1H, m), 3.83 (1H, m), 4.63 (1H, t, J=2.5 Hz), 7.09 (2H, m), 7.25 (1H, d, J=5.0 Hz), 7.58 (1H, d, J=5.0 Hz) and 8.09 (1H, br s).

(e) 1-[4-Benzyloxycarbamoyl]phenoxymethyl-copoly(styrene-1%-divinylbenzene)-2-phenyl-3-[2-(tetrahydro-2H-pyran-2-yloxy)ethyl]-1H-indole 1-[4-Benzyloxycarbamoyl]phenoxymethyl-copoly(styrene-1%-divinylbenzene)-2-bromo-3-[2-(tetrahydro-2H-pyran-2-yloxy)ethyl]-1H-indole (9.8 g; 0.59 mmol/g) was suspended in dry THF (150 ml) and dry nitrogen passed through the solution for one hour. Phenylboronic acid (2.12 g), 2M aqueous $Na_2CO_3$ (10.8 ml) and $Pd(PPh_3)_4$ (668 mg) were added and the solution warmed to reflux for 18 h. After this period the resin was filtered and washed with DMF (4×25 ml) and DCM (4×25 ml), and then resuspended in dry THF (150 ml) and treated with fresh reagents for a further 18 h. The resin was then filtered and washed with DMF (4×25 ml), DCM (4×25 ml), MeOH (4×25 ml) and ether (25 ml). A portion of the recovered resin (100 mg) was then suspended in dry DMF (3.0 ml) containing 5% pyrrolidine and heated to 110° C. for 4 hrs. The resin was filtered off and the solvent removed from the filtrate under reduced pressure to afford 2-phenyl-3-[2-(tetrahydro-2H-pyran-2-yloxy)ethyl]-1H-indole. $^1H$ (360 MHz, $CDCl_3$) δ1.60–2.10 (6H, br m), 3.21 (2H, t, J=11.0 Hz), 3.46 (2H, m), 3.74 (1H, m), 4.03 (1H, m), 4.61 (1H, t, J=3.0 Hz), 7.11–7.17 (2H, m), 7.25 (2H, m), 7.46 (2H, m), 7.66 (3H, m) and 8.17 (1H, br s).

(f) 1-[4-Benzyloxycarbamoyl]phenoxymethyl-copoly(styrene-1%-divinylbenzene)-2-phenyl-1H-indol-3-ylethanol 1-[4-Benzyloxycarbamoyl]phenoxymethyl-copoly(styrene- 1%-divinylbenzene)-2-phenyl-3-[2-(tetrahydro-2H-pyran-2-yloxy)ethyl]-1H-indole (7.87 g) was suspended in a mixture of DCE (125 ml) and ethanol (12.5 ml) containing PPTS (5.83 g) and warmed to 70° C. for 18 h. The resin was then filtered off and washed with DMF (4×25 ml), DCM (4×25 ml), MeOH (4×25 ml) and ether (25 ml). A portion of the recovered resin (100 mg) was then suspended in dry DMF (3.0 ml) containing 5% pyrrolidine and heated to 110° C. for 4 h. The resin was filtered off and the solvent removed from the filtrate under reduced pressure to afford 2-phenyl-1H-indol-3-ylethanol. $^1H$ (360 MHz, $CDCl_3$) δ3.21 (2H, t, J=7.0 Hz), 3.97 (2H, t, J=7.0 Hz), 7.13–7.22 (2H, m), 7.38 (2H, m), 7.45 (2H, m), 7.62 (3H, m) and 8.12 (1H, br s).

(g) 2-Phenyl-3-[2-(piperidin-1-yl)ethyl]-1H-indole

1-[4-Benzyloxycarbamoyl]phenoxymethyl-copoly(styrene- 1%-divinylbenzene)-2-phenyl-1H-indol-3-ylethanol (1.3 g, 0.59 mmol/g) was washed with DCE (5×15 ml) and finally suspended in dry DCE (15 ml). 4- Methyl-2,6-di-tert-butylpyridine (1.95 g) was then added and the resulting suspension cooled to −10° C. Trifluoromethane-sulphonic anhydride (650 μl) was then added and the reaction stirred at −10° C. for 45 min. The reaction was then warmed to room temperature and the resin washed with DCE (3×15 ml) and resuspended in DCE (15 ml). Piperidine (1.3 g) was then added and the mixture agitated by rotation for 4 h. The resin was then filtered and washed with DMF (4×25 ml), DCM (4×25 ml), MeOH (4×25 ml) and ether (25 ml). The recovered resin was then suspended in dry DMF (20 ml) containing 5% pyrrolidine and heated to 110° C. for 4 h. The resin was filtered off and the solvent removed from the filtrate under reduced pressure to afford 2-phenyl-3-[2-(piperidin-1-yl)ethyl]-1H-indole (60 mg). The crude product was purified by flash chromatography ($SiO_2$; DCM/MeOH/$NH_3$ 30:1:0.1) to give the title compound (39 mg). $^1H$ (500 MHz, $CDCl_3$) δ1.45 (2H, m), 1.63 (4H, m), 2.51 (4H, m), 2.68 (2H, dd, J=10.0 and 1.0 Hz), 3.06 (2H, dd, J=10.0 and 1.0 Hz), 7.12 (1H, t, J=5.0 Hz), 7.21 (1H, t, J=5.0 Hz), 7.36 (2H, t, J=3.0 Hz), 7.44 (2H, t, J=3.0 Hz), 7.56 (2H, d, J=3.0 Hz), 7.64 (1H, d, J=1.0 Hz), 8.05 (1H, br s); m/z $ES^+$ 305 $(M+1)^+$.

Method B: 2-Phenyl-3-[2-(4-(2-phenylethyl)piperidin-1-yl)ethyl]-1H-indole

Example 66

Methanesulphonyl chloride (120 μl) was added to a solution of 2-phenyltryptophol (300 mg) and triethylamine (212 μl) in THF (30 ml) at 0° C. The reaction mixture was allowed to warm to room temperature over 20 minutes and filtered. To the filtrate was added 4-(2-phenylethyl)-piperidine hydrochloride (1.0 g), potassium carbonate (1.0 g), water (1.0 ml) and DMF (20.0 ml) and the mixture warmed to 100° C. for 36 hours. The solvent was removed under reduced pressure and the residue partitioned between water (30 ml) and dichloromethane (50 ml). The aqueous layer was extracted using dichloromethane (3×50 ml). The combined organic layers were dried over sodium sulphate, filtered and evaporated. The residue was purified by column chromatography on silica using 25% ethyl acetate in hexane as the eluant followed by trituration in hot methanol to give the desired product (216 mg). $^1$H nmr (360 MHz, DMSO-$d_6$) 1.10–1.25 (3H, m), 1.44–1.54 (2H, m), 1.64–1.72 (2H, m), 1.88–1.98 (2H, m), 2.50–2.64 (4H, m), 2.88–3.02 (4H, m), 6.98–7.03 (1H, m), 7.07–7.20 (4H, m), 7.24–7.29 (2H, m), 7.33–7.40 (2H, m), 7.48–7.54 (2H, m), 7.64–7.67 (2H, m), 11.13 (1H, s). Mass Spec. ES$^+$: m/z for M+1=409.

In accordance with Method A or Method B as described above, the following compounds were prepared:

| Example | Structure | M wt | m/z (M + 1)+ |
|---|---|---|---|
| 1 | 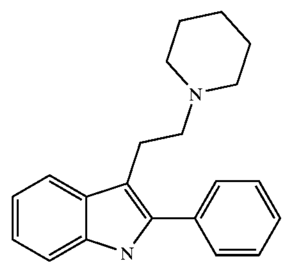 | 304 | 305 |
| 2 | 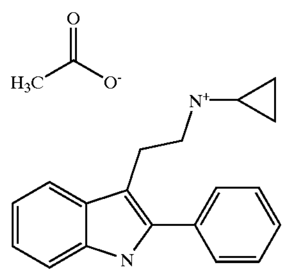 | 276 | 277 |
| 3 | 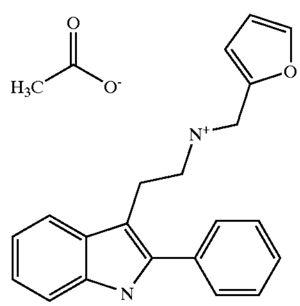 | 316 | 317 |
| 4 | 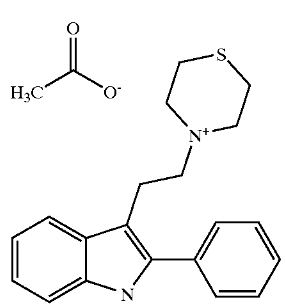 | 322 | 323 |

-continued

| Example | Structure | M wt | m/z (M + 1)+ |
|---|---|---|---|
| 5 | 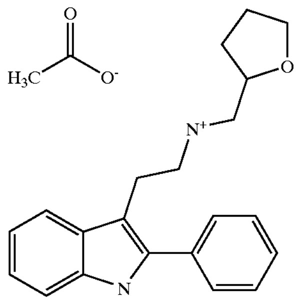 | 320 | 321 |
| 6 | 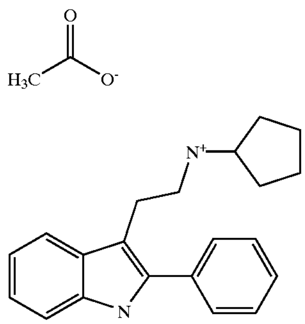 | 304 | 305 |
| 7 | 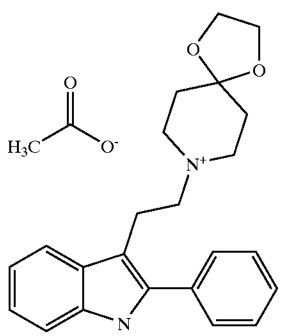 | 362 | 363 |
| 8 | 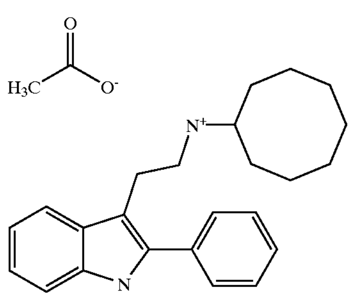 | 347 | 348 |
| 9 | 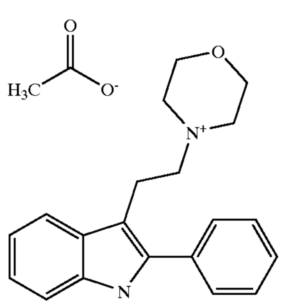 | 306 | 307 |

-continued

| Example | Structure | M wt | m/z (M + 1)+ |
|---|---|---|---|
| 10 | 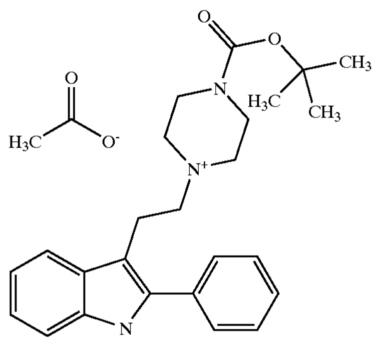 | 406 | 407 |
| 11 | 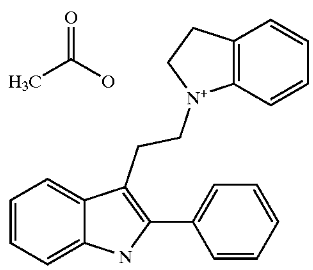 | 338 | 339 |
| 12 | 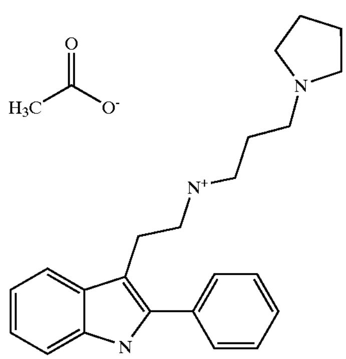 | 348 | 349 |
| 13 | 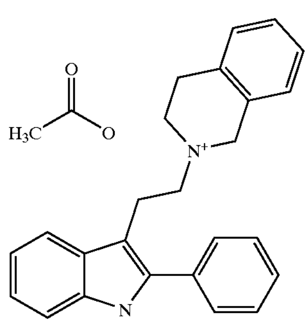 | 352 | 353 |

-continued

| Example | Structure | M wt | m/z (M + 1)+ |
|---|---|---|---|
| 14 | (2-phenylindol-3-yl)ethyl-N-(2-morpholinoethyl)ammonium acetate | 349 | 350 |
| 15 | (2-phenylindol-3-yl)ethyl-N-(1,1-dioxotetrahydrothiophen-3-yl)ammonium acetate | 354 | 355 |
| 16 | (2-phenylindol-3-yl)ethyl-N-(4-acetylpiperazin-1-yl)ammonium acetate | 347 | 348 |
| 17 | (2-phenylindol-3-yl)ethyl-N-[2-(diisopropylamino)ethyl]ammonium acetate | 364 | 365 |
| 18 | (2-phenylindol-3-yl)ethyl-N-(1-benzylpiperidin-4-yl)ammonium acetate | 410 | 411 |

-continued

| Example | Structure | M wt | m/z (M + 1)+ |
|---|---|---|---|
| 19 | 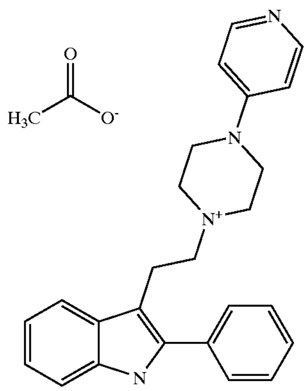 | 383 | 384 |
| 20 | 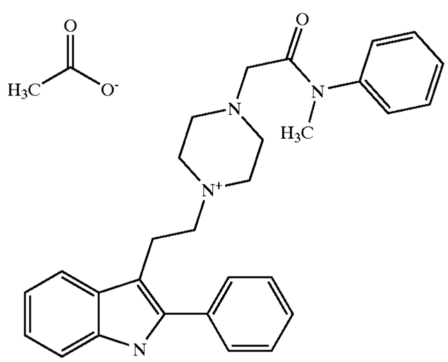 | 453 | 454 |
| 21 | 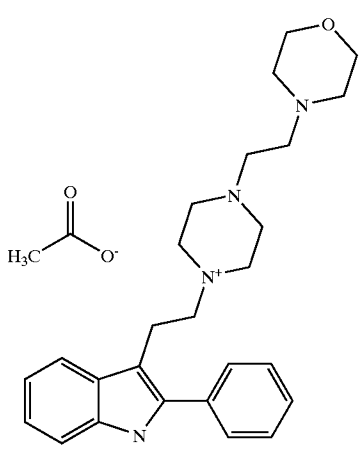 | 419 | 420 |
| 22 | 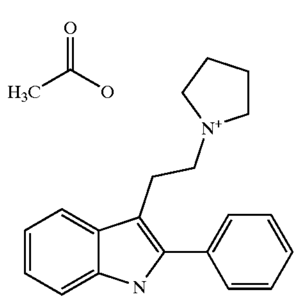 | 290 | 291 |

-continued

| Example | Structure | M wt | m/z (M + 1)+ |
|---|---|---|---|
| 23 | *2-phenylindole with 3-(2-(N-methyl-N-isopropylamino)ethyl) substituent* | 292 | 293 |
| 24 | *2-phenylindole with 3-(2-(N-methyl-N-ethylamino)ethyl) substituent* | 278 | 279 |
| 25 | *2-phenylindole with 3-(2-(N-methyl-N-propylamino)ethyl) substituent* | 292 | 293 |
| 26 | *2-phenylindole with 3-(2-(4-methylpiperazin-1-yl)ethyl) substituent* | 319 | 320 |
| 27 | *2-phenylindole with 3-(2-(4-(2-oxo-2-(pyrrolidin-1-yl)ethyl)piperazin-1-yl)ethyl) substituent* | 417 | 418 |

-continued
| Example | Structure | M wt | m/z (M + 1)+ |
|---|---|---|---|
| 28 | 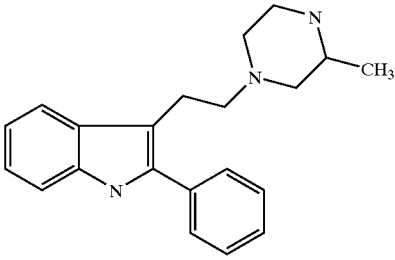 | 319 | 320 |
| 29 | 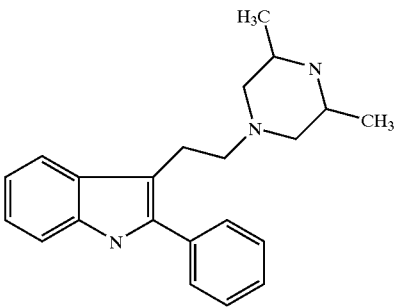 | 333 | 334 |
| 30 | 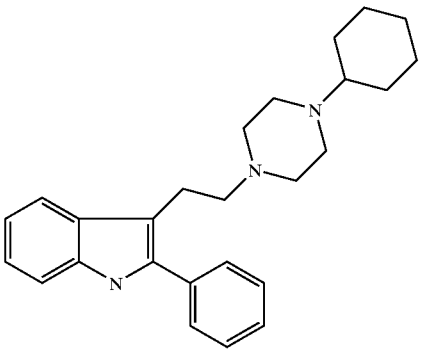 | 388 | 389 |
| 31 | 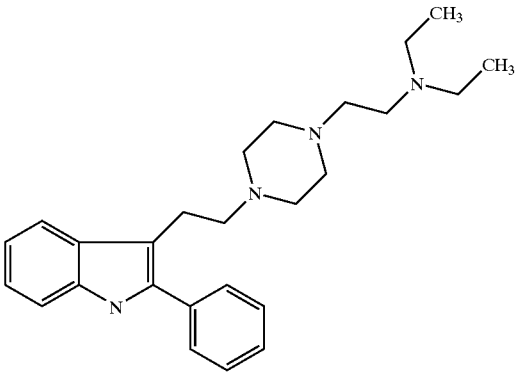 | 405 | 406 |

-continued
| Example | Structure | M wt | m/z (M + 1)+ |
|---|---|---|---|
| 32 | 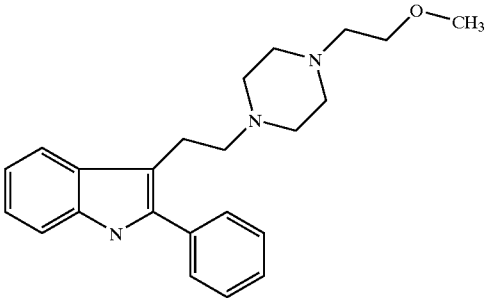 | 364 | 365 |
| 33 | 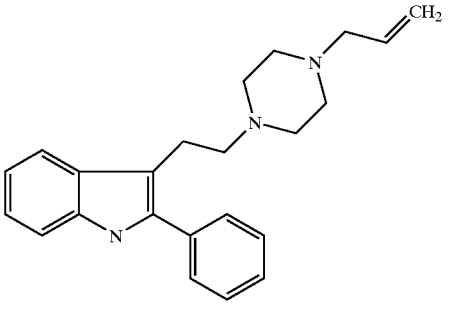 | 345 | 346 |
| 34 | 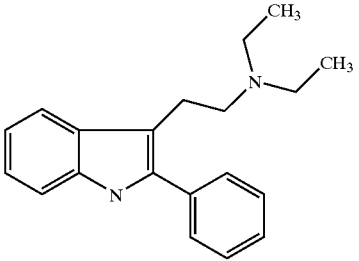 | 292 | 293 |
| 35 | 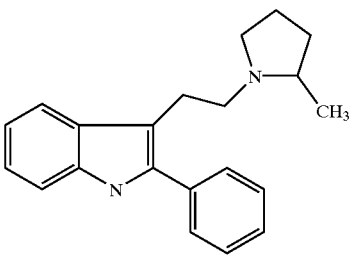 | 304 | 305 |
| 36 | 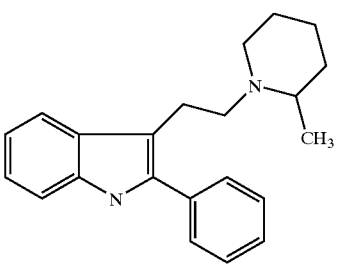 | 318 | 319 |

-continued
| Example | Structure | M wt | m/z (M + 1)+ |
|---|---|---|---|
| 37 | 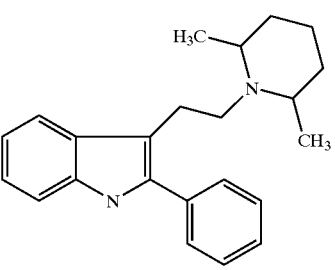 | 332 | 333 |
| 38 | 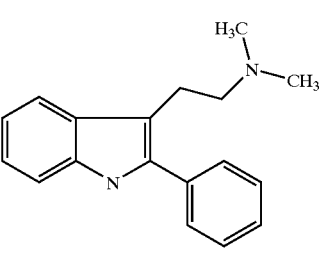 | 264 | 265 |
| 39 | 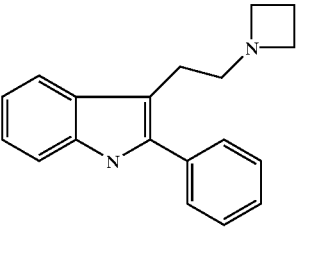 | 276 | 277 |
| 40 | 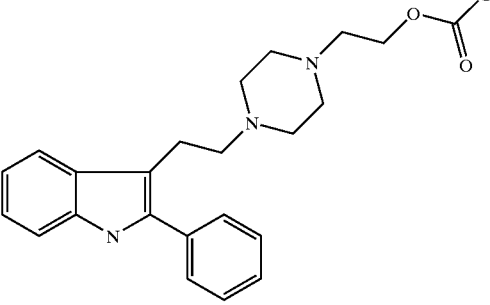 | 392 | 393 |
| 41 | 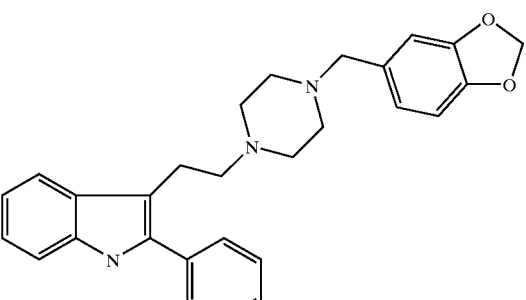 | 440 | 441 |

-continued

| Example | Structure | M wt | m/z (M + 1)+ |
|---|---|---|---|
| 42 | 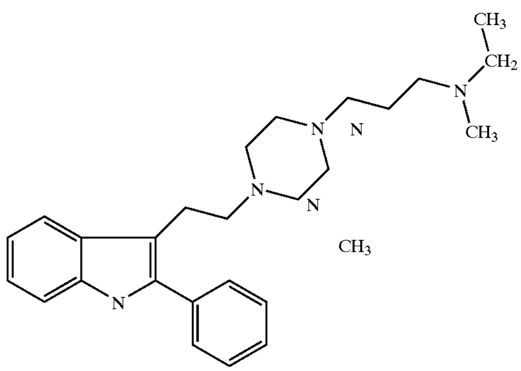 | 391 | 392 |
| 43 | 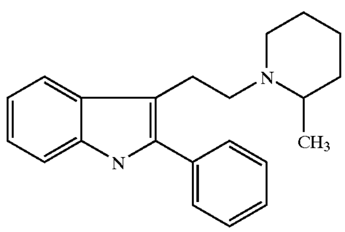 | 318 | 319 |
| 44 | 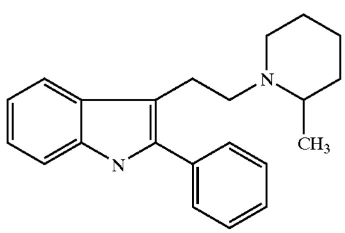 | 318 | 319 |
| 45 | 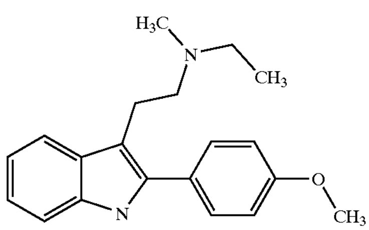 | 308 | 309 |
| 46 | 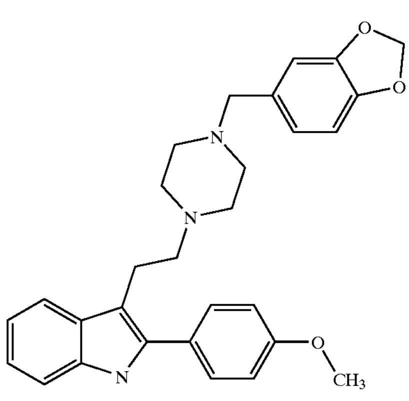 | 470 | 471 |

-continued

| Example | Structure | M wt | m/z (M + 1)+ |
|---|---|---|---|
| 47 | 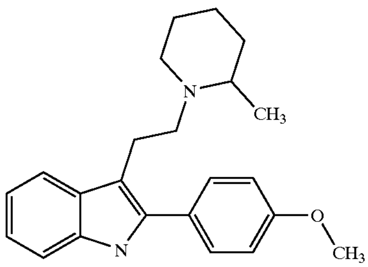 | 348 | 349 |
| 48 | 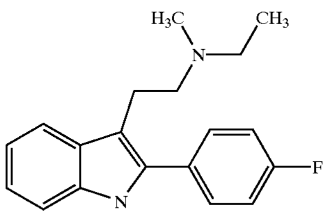 | 296 | 297 |
| 49 | 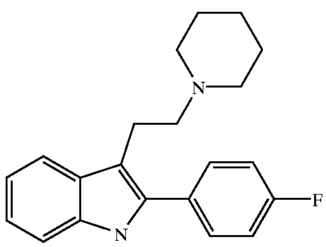 | 322 | 323 |
| 50 | 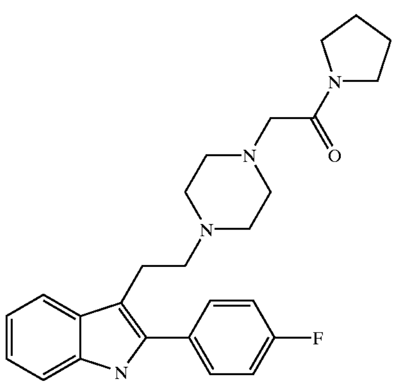 | 435 | 436 |
| 51 | 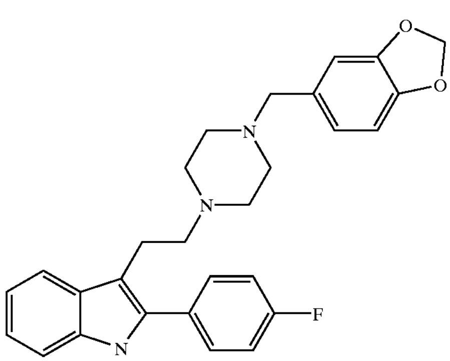 | 458 | 459 |

-continued
| Example | Structure | M wt | m/z (M + 1)+ |
|---|---|---|---|
| 52 | 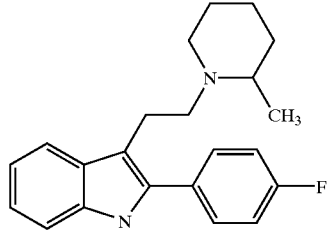 | 336 | 337 |
| 53 | 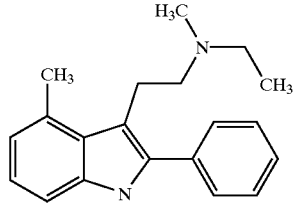 | 292 | 293 |
| 54 | 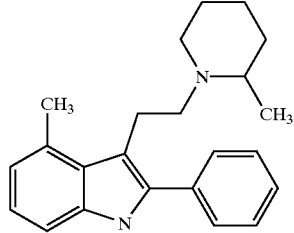 | 332 | 333 |
| 55 | 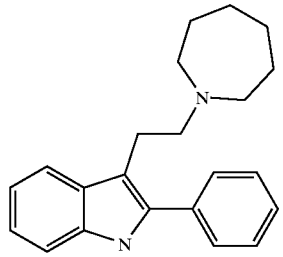 | 318 | 319 |
| 56 | 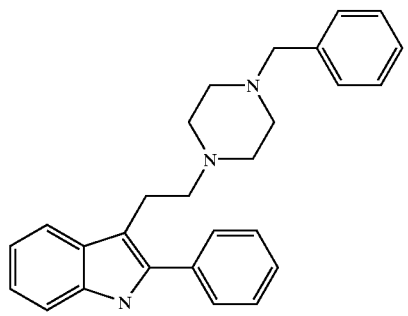 | 396 | 397 |

-continued
| Example | Structure | M wt | m/z (M + 1)+ |
|---|---|---|---|
| 57 | 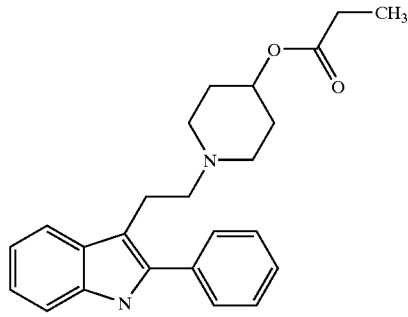 | 362 | 363 |
| 58 | 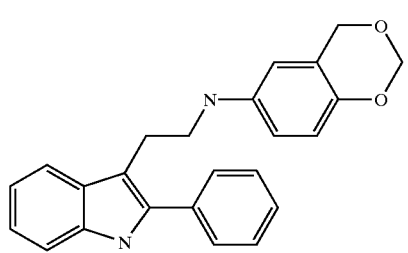 | 370 | 371 |
| 59 | 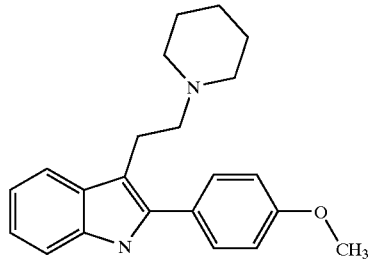 | 334 | 335 |
| 60 | 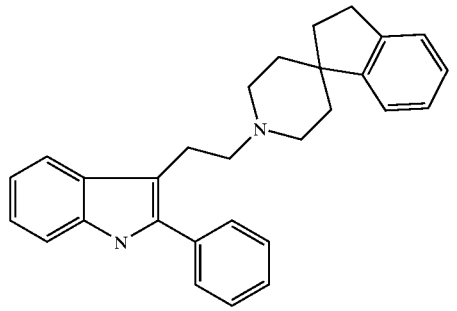 | 407 | 408 |
| 61 | 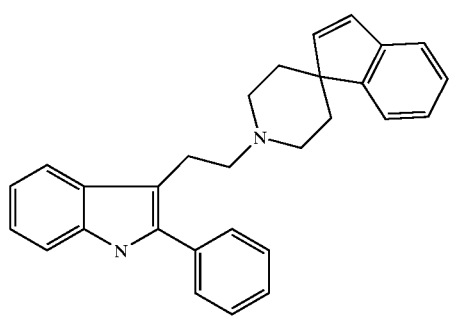 | 405 | 406 |

-continued
| Example | Structure | M wt | m/z (M + 1)+ |
|---|---|---|---|
| 62 | 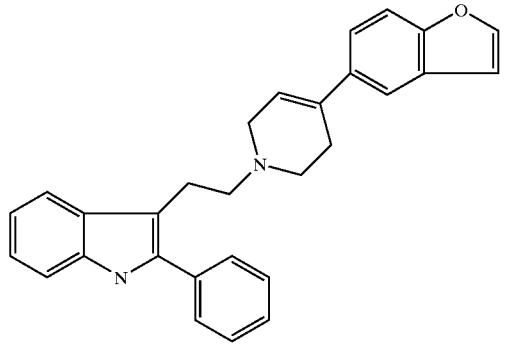 | 419 | 420 |
| 63 | 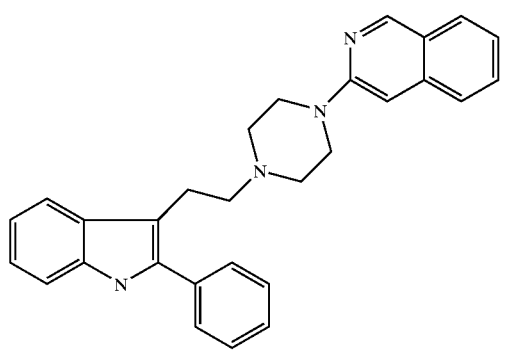 | 433 | 434 |
| 64 | 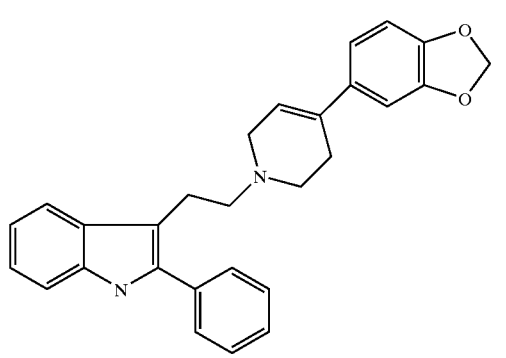 | 423 | 424 |
| 65 | 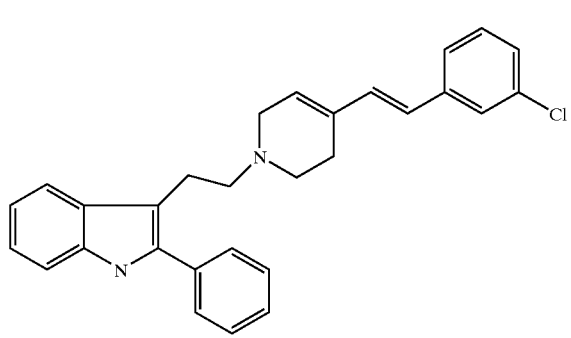 | 455 | 456 |

-continued
| Example | Structure | M wt | m/z (M + 1)+ |
|---|---|---|---|
| 66 | 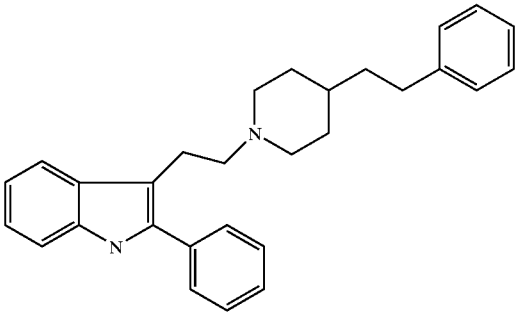 | 409 | 410 |
| 67 | 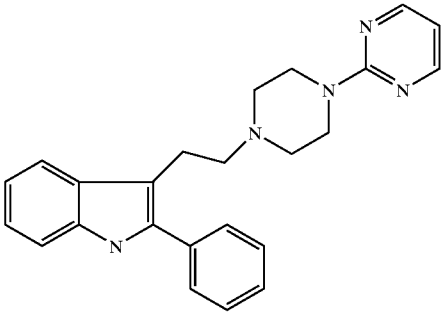 | 384 | 385 |
| 68 | 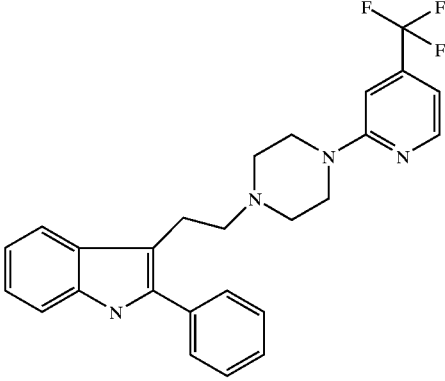 | 451 | 452 |
| 69 | 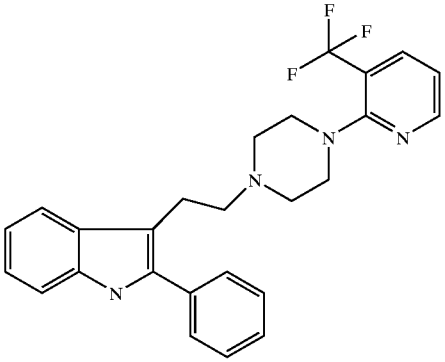 | 451 | 452 |

-continued

| Example | Structure | M wt | m/z (M + 1)+ |
|---|---|---|---|
| 70 | 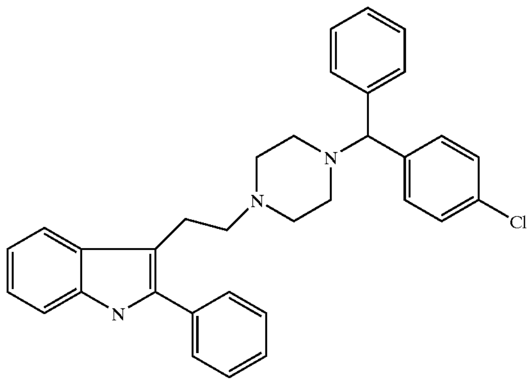 | 506 | 507 |
| 71 | 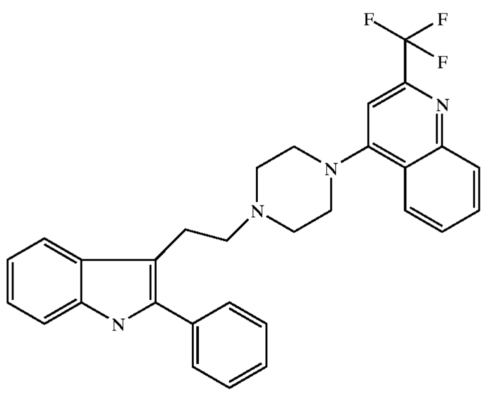 | 501 | 502 |
| 72 | 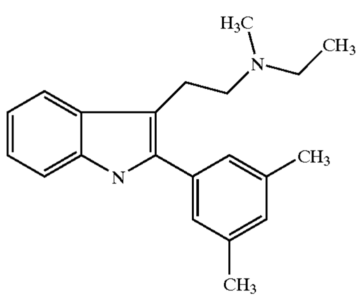 | 306 | 307 |
| 73 | 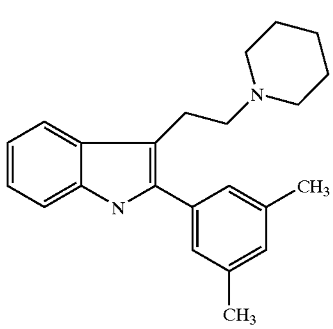 | 332 | 333 |

-continued

| Example | Structure | M wt | m/z (M + 1)+ |
|---|---|---|---|
| 74 | 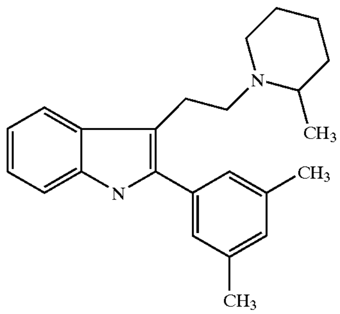 | 347 | 348 |
| 75 | 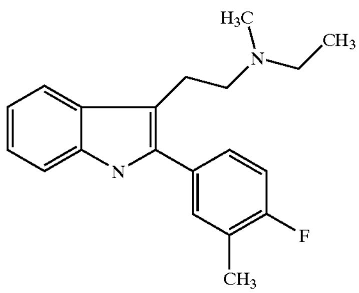 | 310 | 311 |
| 76 | 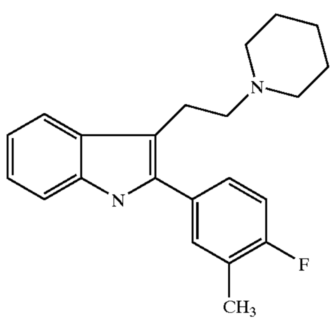 | 336 | 337 |
| 77 | 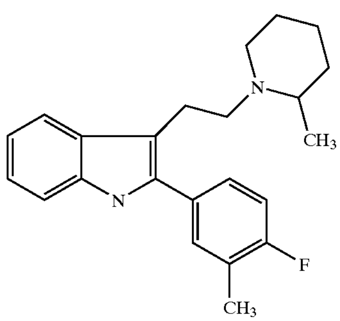 | 350 | 351 |
| 78 | 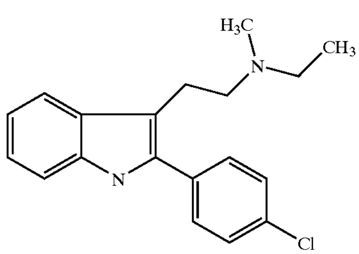 | 313 | 314 |

-continued

| Example | Structure | M wt | m/z (M + 1)+ |
|---|---|---|---|
| 79 | 2-(4-chlorophenyl)-3-(2-piperidin-1-ylethyl)-1H-indole | 339 | 340 |
| 80 | 2-(4-chlorophenyl)-3-[2-(2-methylpiperidin-1-yl)ethyl]-1H-indole | 353 | 354 |
| 81 | N-ethyl-N-methyl-2-[2-(3-methoxyphenyl)-1H-indol-3-yl]ethanamine | 308 | 309 |
| 82 | 2-(3-methoxyphenyl)-3-(2-piperidin-1-ylethyl)-1H-indole | 334 | 335 |
| 83 | 2-(3-methoxyphenyl)-3-[2-(2-methylpiperidin-1-yl)ethyl]-1H-indole | 348 | 349 |

-continued

| Example | Structure | M wt | m/z (M + 1)+ |
|---------|-----------|------|--------------|
| 84 | 2-(4-methylphenyl)-3-[2-(N-methyl-N-ethylamino)ethyl]-1H-indole | 292 | 293 |
| 85 | 2-(4-methylphenyl)-3-[2-(2-methylpiperidin-1-yl)ethyl]-1H-indole | 332 | 333 |
| 86 | 2-phenyl-3-[2-(4-phenethylpiperazin-1-yl)ethyl]-1H-indole | 410 | 411 |
| 87 | 3-[2-(N-ethylamino)ethyl]-2-phenyl-1H-indole | 264 | 265 |
| 88 | 3-[2-(N-methyl-N-ethylamino)ethyl]-2-(4-trifluoromethoxyphenyl)-1H-indole | 362 | 363 |
| 89 | 2-(2-fluorophenyl)-3-[2-(N-methyl-N-ethylamino)ethyl]-1H-indole | 296 | 297 |

-continued

| Example | Structure | M wt | m/z (M + 1)+ |
|---|---|---|---|
| 90 | 2-(3-fluorophenyl)-3-[2-(N-methyl-N-ethylamino)ethyl]indole | 296 | 297 |
| 91 | 2-(4-cyanophenyl)-3-[2-(N-methyl-N-ethylamino)ethyl]indole | 303 | 304 |
| 92 | 2-(3-trifluoromethylphenyl)-3-[2-(N-methyl-N-ethylamino)ethyl]indole | 346 | 347 |
| 93 | 2-(2,4-difluorophenyl)-3-[2-(N-methyl-N-ethylamino)ethyl]indole | 314 | 315 |
| 94 | 2-(3-nitrophenyl)-3-[2-(N-methyl-N-ethylamino)ethyl]indole | 323 | 324 |
| 95 | 2-(4-nitrophenyl)-3-[2-(N-methyl-N-ethylamino)ethyl]indole | 323 | 324 |

-continued
| Example | Structure | M wt | m/z (M + 1)+ |
|---|---|---|---|
| 96 | 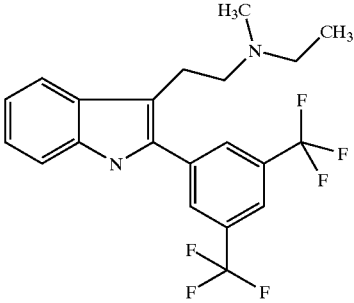 | 414 | 415 |
| 97 | 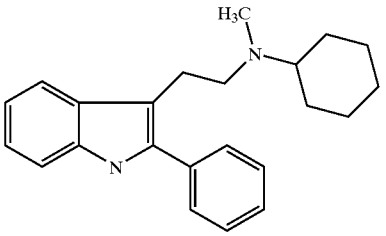 | 332 | 333 |
| 98 | 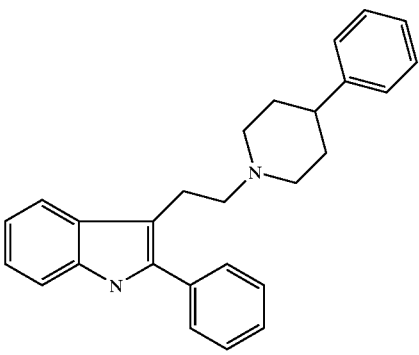 | 381 | 382 |
| 99 | 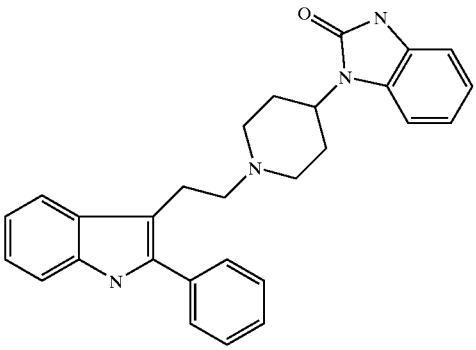 | 437 | 438 |
| 100 | 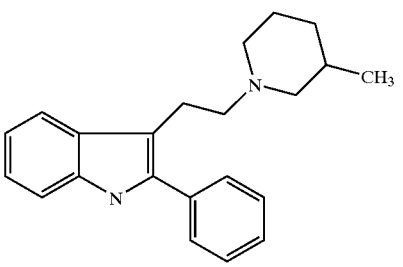 | 318 | 319 |

-continued

| Example | Structure | M wt | m/z (M + 1)+ |
|---|---|---|---|
| 101 | 2-phenyl-3-[2-(2-ethylpiperidin-1-yl)ethyl]-1H-indole | 332 | 333 |
| 102 | 2-phenyl-3-[2-(4-methylpiperidin-1-yl)ethyl]-1H-indole | 318 | 319 |
| 103 | 2-phenyl-3-[2-(3,3-dimethylpiperidin-1-yl)ethyl]-1H-indole | 332 | 333 |
| 104 | 2-phenyl-3-[2-(2-propylpiperidin-1-yl)ethyl]-1H-indole | 347 | 348 |
| 105 | 2-phenyl-3-[2-(5-ethyl-2-methylpiperidin-1-yl)ethyl]-1H-indole | 347 | 348 |

| Example | Structure | M wt | m/z (M + 1)+ |
|---|---|---|---|
| 106 | 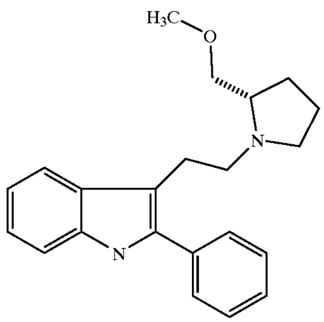 | 334 | 335 |
| 107 | 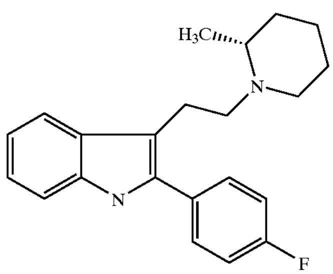 | 336 | 337 |

EXAMPLE 108

5-Bromo-2-phenyl-3-[2-(piperidin-1-yl)ethyl]-1H-indole

1-Phenyl-4-(1-piperidinyl)butan-1-one

γ-Chlorobutyrophenone (25.0 g, 0.14 mol), piperidine (11.65 g, 0.14 mol), potassium carbonate (28.3 g, 0.21 mol) and sodium iodide (30.8 g, 0.21 mol) were dissolved in isopropyl alcohol (150 ml) and heated under reflux for 20 hours. The solvent was removed in vacuo and the residue partitioned between ether and water. The organic phase was washed with brine, dried (sodium sulphate) and evaporated to give a brown oil. Chromatography on silica gel with dichloromethane-methanol-ammonia (98:2:0.2) as the eluent yielded the title compound (9.67 g, 31%) as a brown oil. $\delta_H$ (250 MHz, CDCl$_3$) 1.3–1.5 (2H, m, piperidine H-4), 1.5–1.6 (4H, m, piperidine H-3), 1.8–2.0 (2H, q, J 7, CH$_2$CH$_2$CH$_2$), 2.3–2.5 (6H, m, CH$_2$), 3.0 (2H, t, J 7, COCH$_2$), 7.4–7.6 (3H, m, ArH-4 and H-3), 8.0 (2H, d, J 5, ArH-2); m/z (ES$^+$) 232 ( M$^+$+H).

5-Bromo-2-phenyl-3-[2-(piperidin-1-yl)ethyl]-1H-indole

4-Bromophenylhydrazine hydrochloride (1.45 g, 6.5 mmol) and 1-phenyl-4-(1-piperidinyl)butan-1-one (1.50 g, 6.5 mmol) were dissolved in ethanol (10 ml) and stirred at 25° C. for 4 hours. The solid was filtered and washed with ethanol and ether. The white product was dissolved in trifluoroacetic acid (10 ml) and heated at 70° C. for 2 hours. The reaction mixture was basified with saturated potassium carbonate solution and extracted into ethyl acetate. The organic phase was washed with brine, dried (sodium sulphate) and evaporated to give a yellow oil. Chromatography on silica gel with dichloromethane-methanol-ammonia (98:2:0.2) as eluent yielded the title compound (0.51 g, 20%) as a white solid. Oxalate salt, white crystals, mp 121–122° C. (from methanol/ether) (Found: C, 58.07; H, 5.23; N, 6.01. C$_{21}$H$_{23}$BrN$_2$. C$_2$H$_2$O$_4$. 0.1H$_2$O requires C, 58.14; H, 5.35; N, 5.90%); $\delta_H$ (360 MHz, d$_G$-DMSO) 1.5–1.6 (2H, m, piperidine H-4), 1.7–1.8 (4H, m, piperidine H-3), 3.1–3.3 (8H, m, CH$_2$), 7.2 (1H, dd, J 2 and 8, indole H-6), 7.3 (1H, d, J 8, indole H-7), 7.4 (1H, t, J 7, Ar H-4), 7.5 (2H, t, J 7, Ar H-3), 7.6 (2H, d, J 7, Ar H-2), 7.8 (1H, ds, J 2, indole H-4), 11.6 (1H, br s, indole NH); m/z (ES$^+$) 383 ( M$^+$+H).

The following Examples were made in the same way as Example 108:

EXAMPLE 109

5-Chloro-2-phenyl-3-[2-(piperidin-1-yl)ethyl]-1H-indole

Trifluoroacetic acid salt, white crystals, mp 153–154° C. (from ethanol) (Found: C, 60.03; H, 5.21; N, 6.15. C$_{21}$H$_{23}$ClN$_2$. C$_2$HF$_3$O$_2$. 0.4H$_2$O requires C, 60.04; H, 5.43; N, 6.09%); with the nitrogen protonated, piperidine protons become non-equivalent. $\delta_H$ (360 MHz, d$_G$-DMSO) 1.3–1.5 (1H, m, piperidine H-4), 1.6–1.8 (3H, m, piperidine H-4' and H-3), 1.8–1.9 (2H, d, J 7, piperidine H-3'), 2.9–3.1 and 3.2–3.4 (6H, m, CH$_2$), 3.60 (2H, d J 7, piperidine H-2), 7.15 (1H, dd, J 2 and 9, indole H-6), 7.40 (1H, d, J 9, indole H-7), 7.45 (2H, t, J 7, Ar H-4), 7.55 (2H, t, J 7, Ar H-3), 7.65 (1H, d, J 7, Ar H-2), 7.75 (1H, s, indole H-4), 11.6 (1H, br s, indole-NH); m/z (ES$^+$) 383 (M$^+$+H).

EXAMPLE 110

5-Fluoro-2-phenyl-3-[2-(piperidin-1-yl)ethyl]-1H-indole

Trifluoroacetic acid salt, white crystals mp 141–143° C. (from ethanol) (Found: C, 45.38; H, 3.39; N, 3.99. C$_{21}$H$_{23}$FN$_2$. 3.6 CF$_3$COOH. 0.5 H$_2$O requires C, 45.65; H, 3.75; N, 3.78%); with the nitrogen protonated, piperidine methylene protons become non-equivalent. $\delta_H$ (360 MHz, CDCl$_3$) 1.3–1.4 (1H, m, piperidine H-4), 1.8–2.0 (5H, m, piperidine H-4' and H-3), 2.60–2.65 (2H, t, J 12, piperidine H-2), 3.15 (2H, m, —CH$_2$CH$_2$N), 3.25 (2H, m, —CH$_2$CH$_2$N), 3.60 (2H, d, J 12, piperidine H-2'), 6.9 (1H, ddd, J 2, 9 and 9, indole H-6), 7.2 (1H, dd, J 2 and 9, indole H-4), 7.25 (1H, m, indole H-7), 7.4 (1H, m, Ar H-4), 7.4–7.6 (4H, m, Ar H-3 and H-4); m/z (ES$^+$) 323 (M$^+$+H).

EXAMPLE 111

7-Bromo-2-phenyl-3-[2-(piperidin-1-yl)ethyl]-1H-indole

Oxalate salt, white crystals, mp 206–207° C. (from methanol/ether) (Found: C, 56.97; H, 4.95; N, 5.86. C$_{12}$H$_{23}$BrN$_2$. 1.2C$_2$H$_2$O$_4$ requires C, 57.20; H, 5.21; N, 5.70%); δ$_H$ (360 MHz, d$_G$-DMSO) 1.4–1.6 (2H, m, piperidine H-4), 1.6–1.8 (4H, m, piperidine H-3), 3.0–3.4 (8H, m, CH$_2$), 7.0 (1H, t, J 8, indole H-5), 7.25–7.8 (7H, m, ArH), 11.5 (1H, br s, indole NH): m/z (ES$^+$) 383 (M$^+$+H).

EXAMPLE 112

7- Chloro-2-phenyl-3-[2-(piperidin-1-yl)ethyl]-1H-indole

Oxalate salt, white crystals, mp 178–179° C. (from methanol/ether) (Found: C, 63.81; H, 5.82; N, 6.47. C$_{21}$H$_{23}$ClN$_2$. 1.1C$_2$H$_2$O$_4$ requires C, 63.63; H, 5.80; N, 6.40%); δ$_H$ (360 MHz, d$_G$-DMSO) 1.3 (2H, m, piperidine H-4), 1.7–1.9 (4H, m, piperidine H-3), 3.1–3.4 (8H, m, CH$_2$), 7.05 (1H, t, J 8, indole H-5), 7.2 (1H, d, J 8, indole H), 7.45 (1H, t, J 7, Ar H-4), 7.55 (2H, t, J 7, Ar H-3), 7.65 (3H, m, Ar H-2 and indole H), 11.55 (1H, br s, indole NH); m/z (ES$^+$) 339 (M$^+$+H).

EXAMPLE 113

5-Methyl-2-phenyl-3-[2-(piperidin-1-yl)ethyl]-1H-indole

Oxalate salt, white powder, mp 163–164° C. (from methanol/ether) (Found: C, 68.30; H, 6.52; N, 6.54. C$_{22}$H26N$_2$. 1.25C$_2$H$_2$O$_4$ requires C, 68.28; H, 6.67; N, 6.50%); δ$_H$ (360 MHz, d$_G$-DMSO) 1.3–1.9 (6H, m, piperidine H-3 and H-4), 2.4 (3H, s, ArCH$_3$), 2.8–3.6 (8H, m, CH$_2$), 6.9 (1H, d, J 8, indole H-6), 7.25 (1H, d, J 8, indole H-7), 7.4 (2H, m, indole H-4 and Ar H-4), 7.5 (2H, t, J 8, Ar H-3), 7.6 (2H, d, J 8, Ar H-2), 11.2 (1H, br s, indole NH); m/z (ES$^+$) 319 (M$^+$+H).

EXAMPLE 114

7-Fluoro-2-phenyl-3-[2-(piperidin-1-yl)ethyl]-1H-indole

δ$_H$ (500 MHz, CDCl$_3$) 1.5 (2H, m, piperidine H-4), 1.6–1.9 (4H, m, piperidine H-3), 2.4–2.6 (4H, m, piperidine H-2), 2.8 (2H, m, CH$_2$CH$_2$N), 3.1 (2H, m, CH$_2$CH$_2$N), 6.9 (1H, dd, J 8 and 11, indole H-6), 7.05 (1H, m, indole H-5), 7.4 (2H, m, indole H-4 and Ar H-4), 7.5 (2H, t, J 8, Ar H-3), 7.6 (2H, d, J 8, Ar H-2), 8.2 (1H, br s, indole NH); m/z (ES$^+$) 323 (M$^+$+H).

EXAMPLE 115

4-Fluoro-2-phenyl-3-[2-(piperidin-1-yl)ethyl]-1H-indole

δ$_H$ (360 MHz, CDCl$_3$) 1.40–1.45 (2H, m, piperidine H-4), 1.5–1.8 (4H, m, piperidine H-3), 2.4–2.6 (4H, m, piperidine H-2), 2.6–2.8 (2H, m, CH$_2$CH$_2$N), 3.1–3.2 (2H, m, CH$_2$CH$_2$N), 6.7–6.8 (1H, m, indole H-5), 7.0–7.1 (2H, m, indole H-6 and H-7), 7.4 (1H, m, Ar H-4), 7.5 (2H, t, J 7, Ar H-3), 7.6 (2H, d, J 7, Ar H-2), 8.2 (1H, br s, indole NH); m/z (ES$^+$) 323 (M$^+$+H).

EXAMPLE 116

4-Chloro-2-phenyl-3-[(2-(piperidin-1-yl)ethyl]-1H-indole

δ$_H$ (360 MHz, CDCl$_3$) 1.4–1.8 (6H, m, piperidine H-4 and H-3), 2.6–2.8 (4H, m, piperidine H-2), 2.8–3.0 (2H, m, CH$_2$CH$_2$N), 3.25–3.30 (2H, m, CH$_2$CH$_2$N), 7.05–7.6 (8H, m, ArH), 8.5 (1H, br s, indole NH); m/z (ES$^+$) 339 (M$^+$+H).

EXAMPLE 117

6-Fluoro-2-phenyl-3-[2-(piperidin-1-yl)ethyl]-1H-indole

Oxalate salt, white crystals, mp 214–215° C. (from methanol/ether) (Found: C, 66.85; H, 6.12; N, 7.11. C$_{21}$H$_{23}$FN$_2$. C$_2$H$_2$O$_4$ requires C, 66.98; H, 6.11; N, 6.79%); δ$_H$ (360 MHz, d$_G$-DMSO) 1.45–1.60 (2H, m, piperidine H-4), 1.70–1.80 (4H, m, piperidine H-3), 3.2–3.4 (8H, m, CH$_2$), 6.9 (1H, dt, J 2 and 10, indole H-5), 7.1 (1H, dd, J 2 and 10, indole H-7), 7.4 (1H, t, J 7, Ar H-4), 7.55 (2H, t, J 7, Ar H-3), 7.6–7.7 (3H, m, Ar H-2 and indole H-4), 11.4 (1H, br s, indole NH); m/z (ES$^+$) 323 (M$^+$+H).

EXAMPLE 118

6-Chloro-2-phenyl-3-[2-(piperidin-1-yl)ethyl]-1H-indole

Oxalate salt, white crystals; ml) >230° C. (from methanol/ether) (Found C, 64.52; H, 5.96; N, 6.77. C$_{21}$H$_{23}$ClN$_2$. C$_2$H$_2$O$_4$ requires C, 64.41; H, 5.88; N, 6.53%), δ$_H$ (360 MHz, d$_6$-DMSO) 1.3–1.4 (2H, m, piperidine H-4), 1.5–1.6 (4H, m, piperidine H-3), 2.8–3.1 (8H, m, CH$_2$), 6.9 (1H, d, J8, indol H-5), 7.2–7.3 (2H, m, indole H-7 and Ar H-4), 7.3–7.4 (2H, t, J 7, Ar H-3), 7.4–7.5 (3H, m, indole H-4 and Ar H-2), 11.3 (1H, br s, indole NH); m/z (ES$^+$) 339 (M$^+$+H).

EXAMPLE 119

6-Methyl-2-phenyl-3-[2-(piperidin-1-yl)ethyl]-1-H indole

Oxalate salt, white crystals, mp 112–115° C. (from methanol/ether) (Found: C, 69.07; H, 6.85; N, 6.95. C$_{22}$H$_{26}$N$_2$. C$_2$H$_2$O$_4$. 0.5H$_2$O requires C, 69.04; H, 7.00; N, 6.71%); δ$_H$ (360 MHz, DMSO) 1.45–1.60 (2H, m, piperidine H-4), 1.7–1.8 (4H, m, piperidine H-3), 2.4 (3H, s, ArCH$_3$), 3.1–3.4 (8H, m, CH$_2$), 6.9 (1H, d, J 8, indole H-5), 7.2 (1H, s, indole H-7), 7.4 (1H, m, Ar H-4), 7.5–7.6 (3H, m, indole H-4+Ar H-3), 7.6 (2H, t, J 7, Ar H-2), 11.2 (1H, br s, indole NH); m/z (ES$^+$) 319 (M$^+$+H). The title compound was analysed as a mixture with 25 mol % of 4-methyl-2-phenyl-3-[2-(piperidinyl)ethyl]-1H-indole.

EXAMPLE 120

4-Bromo-2-phenyl-3-[2-(piperidin-1-yl)ethyl]-1H-indole

Oxalate salt, white crytals, mp >230° C. (from methanol/ether) (Found C, 60.62; H, 6.23; N, 6.08: C$_{21}$H$_{23}$BrN$_2$. 0.5C$_2$H$_2$O$_4$. C$_2$H$_5$OH requires C, 60.76; H, 6.37; N, 5.90%); δ$_H$ (360 MHz, d$_G$-DMSO) 1.3–1.4 (2H, m, piperidine H-4), 1.4–1.5 (4H, m, piperidine H-3), 2.6–2.7 (4H, m, piperidine H-2), 2.8 (2H, m, CH$_2$CH$_2$N), 3.1 (2H, m, piperidine H-2), 2.8 (2H, m, CH$_2$CH$_2$N), 3.1 (2H, m, CH$_2$CH$_2$N), 6.9 (1H, t, H 8, indole H-6), 7.1 (1H, d, J 8, indole H), 7.2 (1H, d, J 8, indole H), 7.3 (1H, t, J 7, Ar H-4), 7.4 (2H, t, J 7, Ar H-3), 7.5 (2H, d, J 7, Ar H-2), 11.5 (1H, br s, indole NH); m/z (ES$^+$) 383 (M$^+$+H).

EXAMPLE 121

6-Bromo-2-phenyl-3-[2-(piperidin-1-yl)ethyl]-1H-indole

Oxalate salt, white crystals, mp >230° C. (from methanol/ether) (Found: C, 55.16; H, 5.02; N, 5.73. C$_{21}$H$_{23}$BrN$_2$. 1.4C$_2$H$_2$O$_4$. 1.4H$_2$O requires C, 55.40; H, 5.08; N, 5.43%); δ$_H$ (360 MHz, d$_G$-DMSO) 1.60–1.65 (2H, m, piperidine H-4), 1.8–1.9 (4H, m, piperidine H-3), 3.2–3.4 (8H, m, CH$_2$), 7.3 (1H, dd, J 3 and 8, indole H-5), 7.5 (1H, t, J 7, Ar H-4), 7.6–7.7 (3H, m, indole H-7 and Ar H-3), 7.7–7.8 (3H, m, indole H-4 and Ar H-2), 11.6 (1H, br s, indole NH), m/z (ES$^+$) 383 (M$^+$+H).

EXAMPLE 122

7- Methyl-2-phenyl-3-[2-(piperidin-1-yl)ethyl]-1H-indole

Oxalate salt, white crystals, mp 159–161° C. (from methanol/ether) (Found: C, 68.89; H, 6.81; N, 6.78. C$_{22}$H$_{26}$N$_2$. C$_2$H$_2$O$_4$. 0.6H$_2$O requires 68.75, H, 7.02; N, 6.68%); δ$_H$ (360 MHz, d$_G$-DMSO) 1.8–1.9 (2H, m, piperidine H-4), 2.0–2.1 (4H, m, piperidine H-3), 2.8 (3H, s, ArCH$_3$), 3.4–3.6 (8H, m, CH$_2$), 7.2 (2H, m, indole-H ), 7.7–8.0 (6H, m, ArH), 11.4 (1H, s, indole NH); m/z (ES$^+$) 319 (M$^+$+H).

EXAMPLE 123

5,7-Difluoro-2-phenyl-3-[2-(piperidin-1-yl)ethyl]-1H-indole

Oxalate salt, white crystals, mp 185–187° C. (from methanol/ether) (Found: C, 59.53; H, 5.42; N, 5.31. C$_{21}$H$_{22}$F$_2$N$_2$. 1.5C$_2$H$_2$O$_4$. 0.2C$_2$H$_5$OH. 0.5H$_2$O requires C, 59.36; H, 5.55; N, 5.67%); δ$_H$ (360 MHz, d$_G$-DMSO) 1.4–1.8 (6H, m, piperidine H-4 and H-3), 3.2–3.4 (8H, m, CH$_2$), 7.0 (1H, dt, J 2 and 10), 7.4 (1H, dd, J 2 and 10), 7.45 (1H, t, J 7, Ar H-4), 7.55 (2H, t, J 7, Ar H-3), 7.7 (2H, d, J 7, Ar H-2), 11.8 (1H, s, indole NH); m/z (ES$^+$) 341 (M$^+$+H).

EXAMPLE 124

2,6-Diphenyl-3-[2-(piperidin-1-yl)ethyl]-1H-indole

Oxalate salt, white crystals, mp 129–131° C. (from methanol/ether) (Found: C, 72.50; H, 6.26; N, 6.00. C$_{27}$H$_{28}$N$_2$. C$_2$H$_2$O$_4$. 0.5H$_2$O requires C, 72.63; H, 6.52; N, 5.84%); δ$_H$ (360 MHz, dr-DMSO) 1.5–1.6 (2H, m, piperidine H-4), 1.7–1.8 (4H, m, piperidine H-3), 3.1–3.4 (8H, m, CH$_2$), 7.2–7.8 (13H, m, Ar-H ), 11.4 (1H, br s, indole NH); m/z (ES$^+$) 381 (M$^+$+H).

EXAMPLE 125

2,4-Diphenyl-3-[2-(piperidin-1-yl)ethyl-1H-indole

Oxalate salt, white crystals, mp 142–143° C. (from methanol/ether) (Found: C, 70.81; H, 6.18; N, 5.73. C$_{27}$H$_{28}$N$_2$. 1.25C$_2$H$_2$O$_4$. 0.4H$_2$O requires C, 70.82; H, 6.31; N, 5.60%); δ$_H$ (360 MHz, d$_G$-DMSO) 1.3–1.4 (2H, m, piperidine H-4), 1.4–1.5 (4H, m, piperidine H-3), 2.3–2.6 (6H, m, CH$_2$), 2.9 (2H, m, CH$_2$CH$_2$N), 6.85 (1H, d, J 7, indole H), 7.2 (1H, t, J 7, indole H-6), 7.4–7.7 (11H, m, ArH), 11.6 (1H, s, indole NH); m/z (ES$^+$) 381 (M$^+$+H).

EXAMPLE 126

4- Methoxy-2-phenyl-3-[2-(piperidin-1-yl)ethyl]-1H-indole

Off-white solid, mp 260–262° C.; δ$_H$ (360 MHz, d$_G$-DMSO) 1.74 (6H, m, 3×CH$_2$), 2.90 (2H, m, NCH$_2$), 3.30 (4H, m, 2×NCH$_2$), 3.50 (2H, m, ArCH$_2$), 3.91 (3H, s, OCH$_3$), 6.53 (1H, d, J 8, CH), 7.02 (1H, d, J 8, CH), 7.11 (1H, dd, J 8 and 8, CH), 7.41 (1H, dd, J 8 and 8, CH), 7.52 (2H, dd, J 8 and 8, 2×CH) and 7.59 (2H, d, J 8, 2×CH); m/z (ES$^+$) 335 (M$^+$+H).

EXAMPLE 127

7- Methoxy-2-phenyl-3-[2-(piperidin-1-yl)ethyl]-1H-indole

Oxalate salt, white solid, mp 203–205° C. (Found: C, 66.2; H, 6.0; N, 7.2; C$_{24}$H$_{28}$N$_2$O$_5$ requires C, 67.9; H, 6.6; N, 6.6%); δ$_H$ (360 MHz, d$_G$-DMSO) 1.56 (2H, m, CH$_2$), 1.72 (4H, m, 2×NCH$_2$CH$_2$), 3.18 (8H, m, 3×NCH$_2$ and ArCHO, 3.92 (3H, s, OCH$_3$), 6.71 (1H, d, J8, CH), 6.99 (1H, dd, J 8 and 8, CH), 7.23 (1H, d, J 8, CH), 7.39 (1H, dd, J 8 and 8, CH), 7.50 (2H, dd, J 8 and 8, 2×CH) and 7.63 (2H, d, J 8, 2×CH); m/z (ES$^+$) 335 (M$^+$+H).

EXAMPLE 128

2-Phenyl-3-[2-(piperidin-1-yl)prop-1-yl]-1H-indole a) 3-[2-(Piperidin-1-yl)prop-1-yl]-1H-indole To a solution of indole-3-acetone (5.0 g, 29 mmol) in anhydrous 1,2-dichloroethane (100 ml) under an atmosphere of nitrogen was added piperidine (2.9 ml, 29 mmol), and glacial acetic acid (1.66 ml, 29 mmol) followed by sodium triacetoxyborohydride (6.8 g, 32 mmol). On complete addition the reaction mixture was stirred at room temperature for 17 hours. The mixture was basified by the addition of a saturated solution of sodium hydrogen carbonate, the layers were separated and the organic layer dried over anhydrous magnesium sulfate, filtered and evaporated in vacuo. The residue was purified by column chromatography on silica elution with 5% CH$_3$OH in CH$_2$Cl$_2$+0.5% 0.88 ammonia to give the title product (3 g, 43%); δ$_H$ (360 MHz; CDCl$_3$) 0.99 (3H, d, J 6.5 Hz, —CH$_3$), 1.43–1.51 (2H, m, aliphatics), 1.60–1.69 (4H, m, aliphatics), 2.56–2.70 (5H, m, aliphatics+ indole CH$_A$CH$_B$), 2.87–2.99 (1H, m, indole CH$_A$H$_B$CH (piperidine)), 3.12 (1H, dd, J 13.9 and 3.6 Hz, indole CH$_A$CH$_B$), 7.02 (1H, d, J 1.9 Hz, indole H2), 7.09 (1H, m, indole H6), 7.17 (1H, m, indole H5), 7.34 (1H, d, J 8.0 Hz, indole H7), 7.61 (1H, d, J 7.6 Hz, indole H4), 8.01 (1H, bs, indole NH); m/z (ES$^+$) 243 (M$^+$+H, 100%).

b) 1-tert-Butoxycarbonyl-3-[2-(piperidin-1-yl)prop-1-yl]-1H-indole

To a solution of 3-[2-(piperidin-1-yl)prop-1-yl]-1H-indole (3.0 g, 12.4 mmol) in anhydrous dichloromethane under an atmosphere of nitrogen was added di-tert-butyl dicarbonate (3.0 g, 13.6 mmol) followed by 4-dimethylaminopyridine (1.66 g, 13.6 mmol). On complete addition the reaction mixture was stirred at room temperature for 3 hours then evaporated in vacuo. The residue was purified by column chromatography on silica eluting with 2% CH$_3$OH in CH$_2$Cl$_2$+0.5% 0.88 ammonia to give the title compound (3.6 g, 85%); δ$_H$ (360 MHz; CDCl$_3$) 1.00 (3H, d, J 6.5 Hz, —CH$_3$), 1.43–1.52 (2H, m, aliphatics), 1.59–1.65 (4H, m, aliphatics), 1.67 (9H, S, O$_2$C(CH$_3$)$_3$), 2.54 (1H, dd, J 13.9 and 9.4 Hz, indole CH$_A$H$_B$), 2.59–2.65 (4H, m, aliphatics), 2.88–2.97 (1H, m, indole CH$_A$H$_B$CH), 3.01 (1H, dd, J 13.9 and 3.7 Hz, indole CH$_A$H$_B$), 7.19–7.34 (2H, m, indole H5+H6), 7.43 (1H, s, indole H2), 7.53 (1H, d, J=7.7 Hz, indole H4), 8.10 (1H, broad doublet, indole H7); m/z (ES$^+$) 343 (M$^+$+H, 100%).

c) 2-Bromo-1-tert-butoxycarbonyl-3-[2-(piperidin-1-yl) prop-1-yl]-1H-indole

To a solution of 2,2,6,6-tetramethylpiperidine (5.3 ml, 31.6 mmol) in anhydrous tetrahydrofuran (50 ml) cooled to −78° C. under an atmosphere of nitrogen was added in a dropwise manner n-butyllithium (12.6 ml of a 2.5M solution in hexanes, 31.6mmol). On complete addition the reaction mixture was allowed to warm to 0° C. and stirred at this temperature for 5 minutes. Re-cooled to −78° C. and a solution of the 1-tert-butoxycarbonyl-3-[2-(piperidin-1-yl) prop-1-yl]-1H-indole in anhydrous tetrahydrofuran (50 ml) added via a cannula at such a rate that the temperature did not rise above −50° C. On complete addition the reaction mixture was stirred at −78° C. for 4 hours then 1,2-dibromotetrafluoroethane (3.78 ml, 31.6 mmol) added; the reaction mixture was allowed to warm to room temperature and stirred for 18 hours. The solvent was removed in vacuo and the residue purified by column chromatography on silica eluting with 2% CH$_3$OH in CH$_2$Cl$_2$+0.5% 0.88 ammonia to give the title compound (1.5 g, 34%); δ$^H$ ($^{360}$ MHz; CDCl$_3$) 1.32 (3H, d, J 6.7 Hz, CH$_3$), 1.71 (9H, s, O$_2$C(CH$_3$)$_3$), 2.99–3.05 (1H, m, indole CH$_A$H$_B$), 3.55–3.67 (1H, m, indole CH$_A$H$_B$CH), 3.74 (1H, d, J 13.2 Hz, indole CH$_A$H$_B$), 7.26–7.33 (2H, m, indole H5+H6), 7.92 (1H, dd, J 6.6 and 3.7 Hz, indole H4), 8.05 (1H, d, J 5.8 and 2.2 Hz, indole H7), piperidine protons very broad and merged into baseline; m/z (ES$^+$) 421/423 (M$^+$+H, 100%).

d) 2-Phenyl-3-[2-(piperidin-1-yl)prop-1-yl]-1H-indole

To a solution of the 2-bromo-1-tert-butoxycarbonyl-3-[2-(piperidin-1-yl)prop-1-yl]-1H-indole (750 mg, 1.8 mmol) and phenyl boronic acid (326 mg, 2.6 mmol) in a mixture of ethanol (25 ml) and toluene (25 ml) was added sodium carbonate (4.4 ml of a 1.0M solution in water, 4.4 mmol), lithium chloride (227 mg, 5.3 mmol), and tetrakis (triphenylphosphine)-palladium(0) (100 mg, 0.08 mmol) sequentially. The reaction mixture was heated to reflux under an atmosphere of nitrogen for 65 hours. The reaction was cooled and evaporated in vacuo; the residue was azeotroped with toluene (2×50 ml). The residue was dissolved in anhydrous dichloromethane (50 ml) and trifluoroacetic acid (5 ml, 65 mmol) added and the mixture stirred at room temperature for 19 hours. The reaction mixture was basified by the addition of a saturated solution of sodium hydrogen carbonate, the organic layer was separated and dried over anhydrous magnesium sulfate, filtered and evaporated in vacuo. The product was purified by preparative TLC eluting with 5% CH$_3$OH in CH$_2$Cl$_2$+0.5% 0.88 ammonia and the oxalate salt formed from EtOH/Et2O to give the title compound (71 mg, 10%); mp 240° C.; (Found: C, 71.58; H, 7.01; N, 7.01. C$_{22}$H$_{26}$N$_2$. 0.9(CO$_2$H)$_2$ requires C, 71.58; H, 7.00; N, 7.03%); δ$^H$ (360 MHz; d$_6$-DMSO) 0.96 (3H, d, J 6.5 Hz, —CH$_3$), 1.44–1.64 (2H, m, aliphatics), 1.70–1.88 (4H, m, aliphatics), 3.04–3.30 (5H, m, aliphatics), 3.38–3.52 (2H, m, indole CH$_A$H$_B$+indole CH$_A$H$_B$CH), 7.04 (1H, t, J 7.7 and 7.1 Hz, indole H5), 7.13 (1H, t, J 7.7 and 7.3 Hz, indole H6), 7.38 (1H, d, J 8.0 Hz, indole H4), 7.42 (1H, d, J 7.3 Hz, indole H7), 7.53 (2H, t, J 7.8 and 7.5 Hz, aromatics), 7.65–7.69 (3H, m, aromatics), 11.34 (1H, s, indole NH); m/z (ES$^+$) 319 (M$^+$+H, 100%).

EXAMPLES 129 TO 231

Method C: 2-[3,5-Bis(trifluoromethyl)phenyl]-3-[2-(N-methyl-N-isopropylamino)ethyl]-1H-indole
(Example 129)

(a) 1-tert-Butoxycarbonyl-2-[3,5-bis(trifluoromethyl) phenyl]-3-[2-(tetrahydro-2H-pyran-2-yloxy)ethyl]-1H-indole To a degassed solution of 1-tert-butoxycarbonyl-2-bromo-3-[2-(tetrahydro-2H-pyran-2-yloxy)ethyl]-1H-indole (2.0 g), 3,5-bis(trifluoromethyl)phenylboronic acid (2.43 g) and Na$_2$CO$_3$ (aq., 2N, 8.8 ml) in tetrahydrofuran was added tetrakis(triphenylphosphine)-palladium(0) (0.55 g). The resulting solution was then warmed to reflux for 18 h, cooled to room temperature and partitioned between ethyl acetate and water. The organic layer was separated, washed with water and brine, dried over MgSO$_4$, filtered and the solvent removed under reduced pressure. The residue was purified by flash chromatography (SiO$_2$; 3–5% ethyl acetate/hexanes) to afford the title compound (2.1 g). $^1$H NMR (CDCl$_3$) δ1.23 (s, 9H), 1.45–1.71 (br m, 6H), 2.82 (t, 2H, J=7.2 Hz), 3.37 (m, 1H), 3.61 (m, 2H), 3.98 (m, 1H), 4.50 (t, 1H, J=3.5 Hz), 7.30 (t, 1H, J=7.0 Hz), 7.41 (t, 1H, J=7.0 Hz), 7.60 (d, 1H, J=10.0 Hz), 7.89 (s, 1H), 7.91 (s, 2H), 8.27 (d, 1H, J=10.0 Hz).

(b) 1-tert-Butoxycarbonyl-2-[3,5-bis(trifluoromethyl) phenyl]-3-(2-hydroxyethyl)-1H-indole PPTS (95 mg) was added to a stirred solution of 1-tert-butoxycarbonyl-2-[3,5-bis(trifluoromethyl)phenyl]-3-[2-(tetrahydro-2H-pyran-2-yloxy)ethyl]-1H-indole (2.1 g) in ethanol (50 ml) and warmed to 50° C. for 3 h. The reaction mixture was allowed to cool to room temperature, poured into brine (80 ml) and extracted into diethyl ether. The organic layers were separated, dried over MgSO$_4$, filtered and the solvent removed under reduced pressure to give a clear oil which crystallized on standing (1.67 g). $^1$H NMR (CDCl$_3$) δ1.23 (s, 9H), 2.79 (t, 2H, J=7.2 Hz), 3.86 (m, 2H), 7.27 (t, 1H, J=7.0 Hz), 7.34 (t, 1H, J=7.0 Hz), 7.60 (d, 1H, J=10.0 Hz), 7.90 (s, 3H), 8.28 (d, 1H, J=10.0 Hz).

(c) 2-[3,5-Bis(trifluoromethyl)phenyl]-3-[2-(N-methyl-N-isopropylamino)ethyl]-1H-indole Trifluoromethanesulphonic anhydride (10 ml) was added to a cooled (−78° C.) solution of 1-tert-butoxycarbonyl-2-[3,5-bis(trifluoromethyl)-phenyl]-3-(2-hydroxyethyl)-1H-indole (20 mg) in dry dichloromethane (1.0 ml). After 30 min N-methylisopropylamine (100 ml of a 1.0 mmol solution in dichloromethane) was added. The reaction was allowed to warm to room temperature overnight and was then treated with methylisocyanate polystyrene resin (100 mg @ 1.0 mmol/g). The reaction solution was filtered and the solvent removed under reduced pressure. The residue was taken up in 0.2N NaO Me/methanol (1.0 ml) and warmed to 45° C. for two hours. The solvent was removed under reduced pressure and the title compound recovered by ion exchange chromatography (SCX, 2N NH$_3$/MeOH), m/z (m+H)$^+$429.

In accordance with Method C as described above, the following compounds were prepared:

| Example | Structure | mol weight | m/z (M + 1) + |
|---------|-----------|------------|---------------|
| 129 | 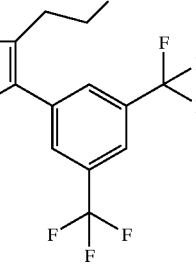 | 428.42 | 429 |
| 130 | 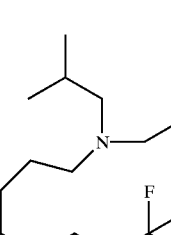 | 484.53 | 486 |
| 131 | 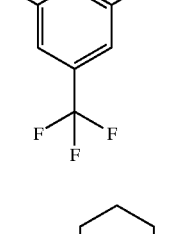 | 496.54 | 498 |
| 132 | 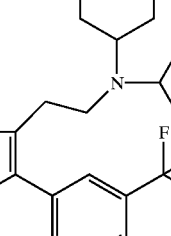 | 442.45 | 443 |

-continued

| Example | Structure | mol weight | m/z (M + 1) + |
|---|---|---|---|
| 133 | 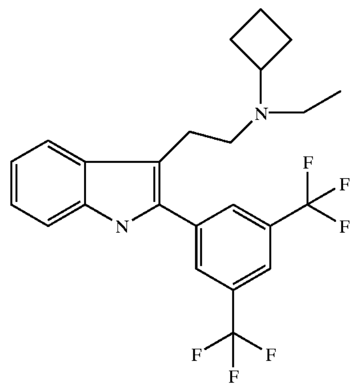 | 454.46 | 455 |
| 134 | 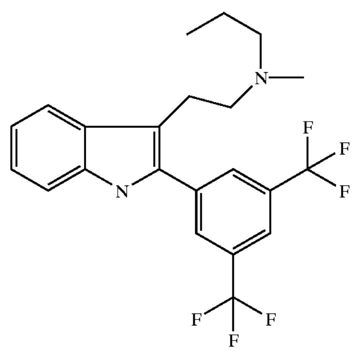 | 428.42 | 429 |
| 135 | 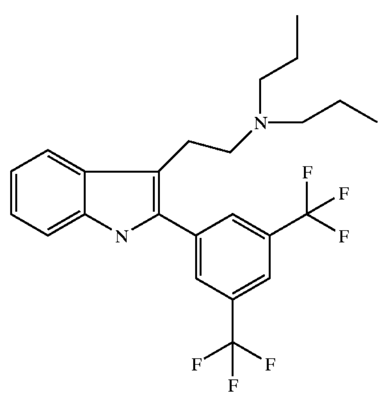 | 456.48 | 457 |
| 136 | 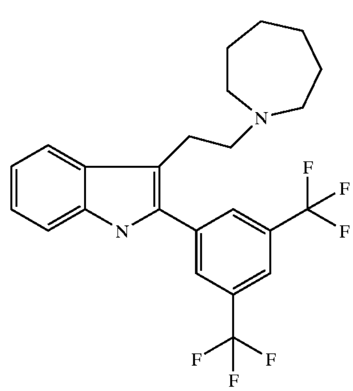 | 454.46 | 455 |

-continued

| Example | Structure | mol weight | m/z (M + 1) + |
|---------|-----------|------------|---------------|
| 137 | 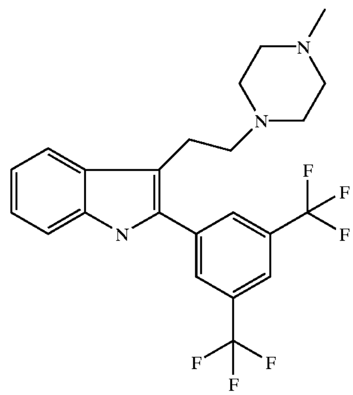 | 455.45 | 456 |
| 138 | 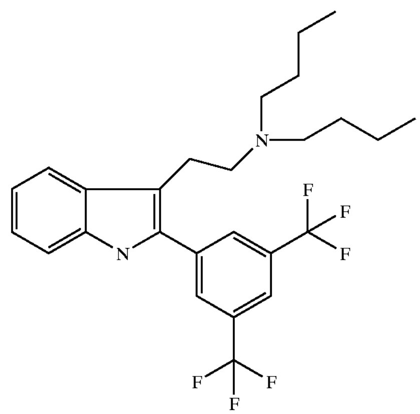 | 484.53 | 486 |
| 139 | 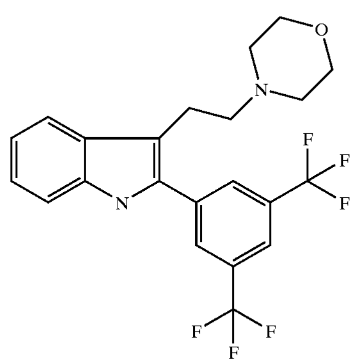 | 442.41 | 443 |
| 140 | 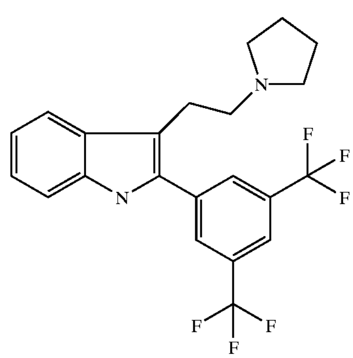 | 426.41 | 427 |

-continued
| Example | Structure | mol weight | m/z (M + 1) + |
|---|---|---|---|
| 141 | 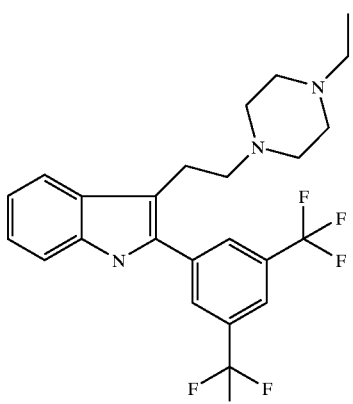 | 469.48 | 470 |
| 142 | 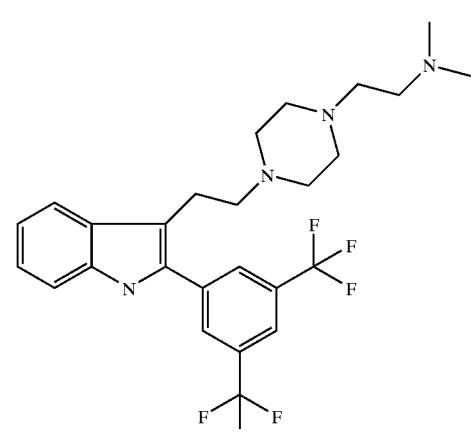 | 512.55 | 514 |
| 143 | 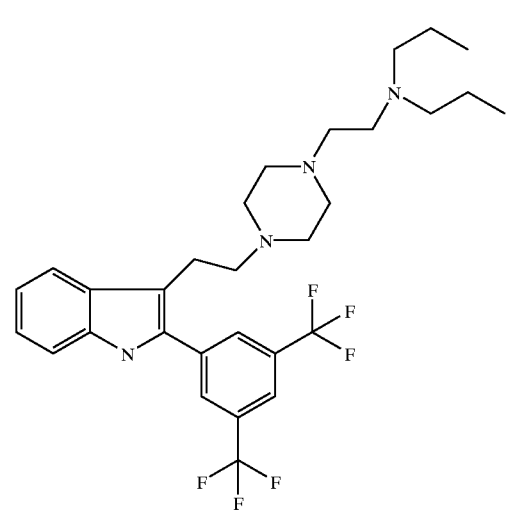 | 568.65 | 570 |

-continued
| Example | Structure | mol weight | m/z (M + 1) + |
|---|---|---|---|
| 144 | 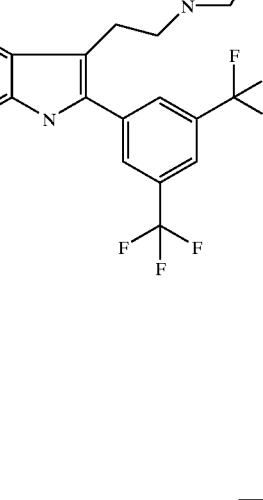 | 499.50 | 501 |
| 145 | 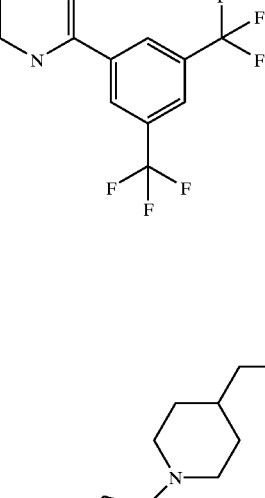 | 554.58 | 556 |
| 146 | 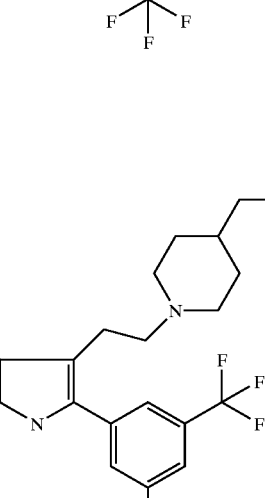 | 530.56 | 532 |

-continued

| Example | Structure | mol weight | m/z (M + 1) + |
| --- | --- | --- | --- |
| 147 | 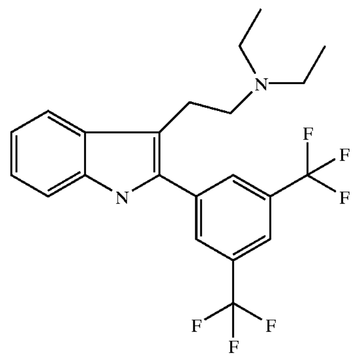 | 428.42 | 429 |
| 148 | 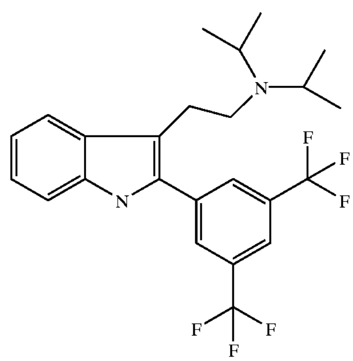 | 456.48 | 457 |
| 149 | 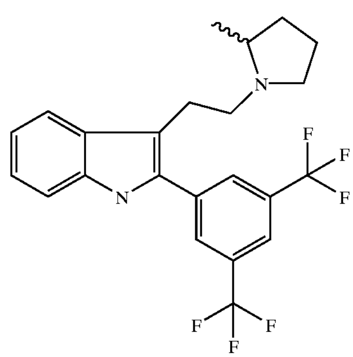 | 440.44 | 441 |
| 150 | 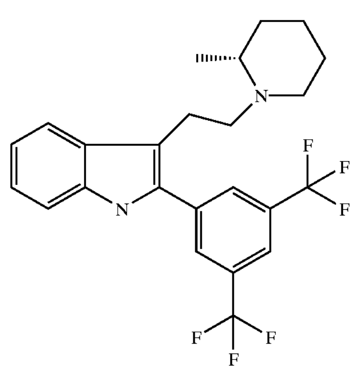 | 454.46 | 455 |

-continued

| Example | Structure | mol weight | m/z (M + 1) + |
|---|---|---|---|
| 151 | 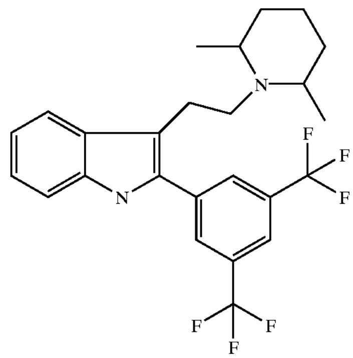 | 468.49 | 469 |
| 152 | 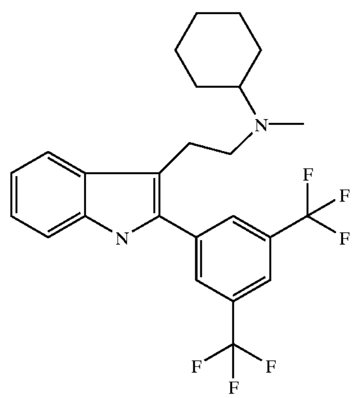 | 468.49 | 469 |
| 153 | 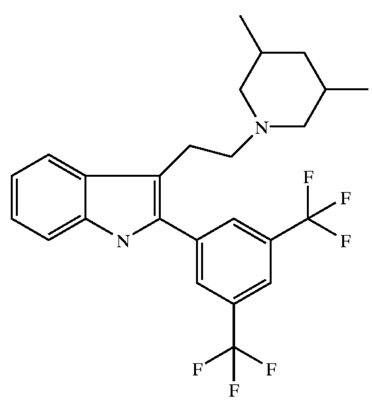 | 468.49 | 469 |
| 154 | 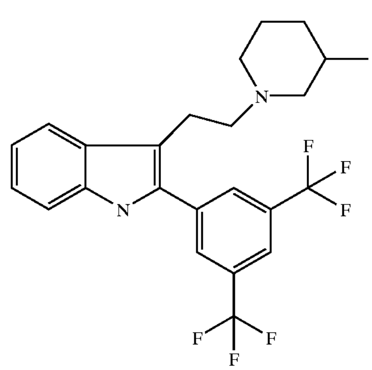 | 454.46 | 455 |

-continued

| Example | Structure | mol weight | m/z (M + 1) + |
|---|---|---|---|
| 155 | 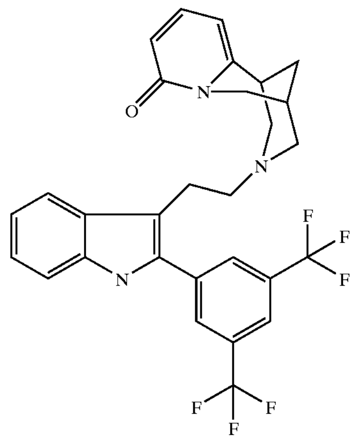 | 545.53 | 547 |
| 156 | 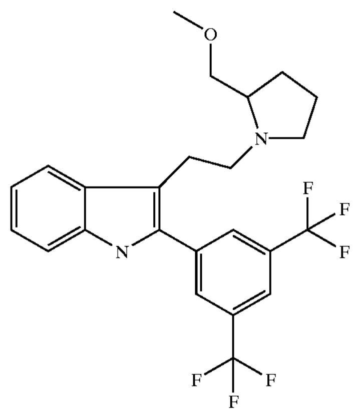 | 470.46 | 471 |
| 157 | 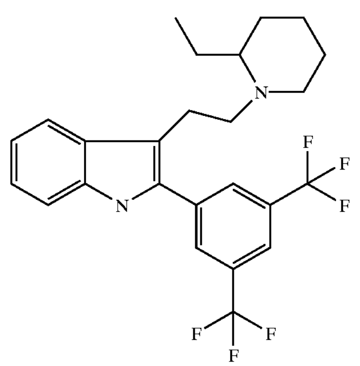 | 468.49 | 469 |
| 158 | 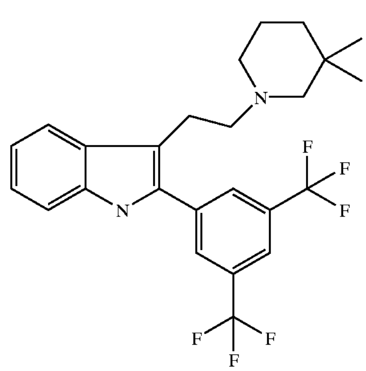 | 468.49 | 469 |

-continued
| Example | Structure | mol weight | m/z (M + 1) + |
|---|---|---|---|
| 159 | 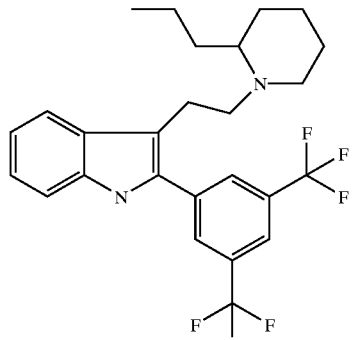 | 482.52 | 484 |
| 160 | 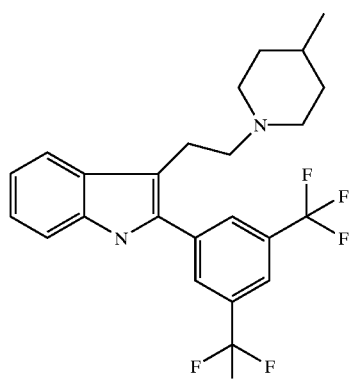 | 454.46 | 455 |
| 161 | 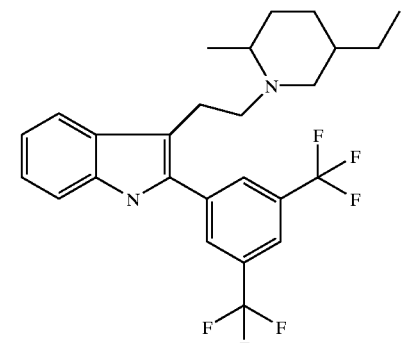 | 482.52 | 484 |
| 162 | 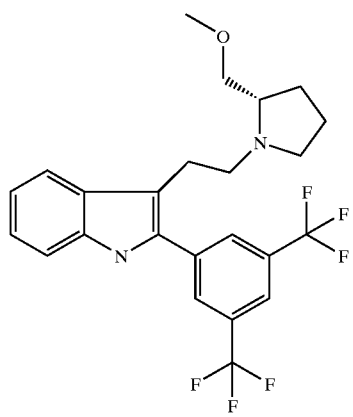 | 470.46 | 471 |

-continued

| Example | Structure | mol weight | m/z (M + 1) + |
|---------|-----------|------------|---------------|
| 163 | 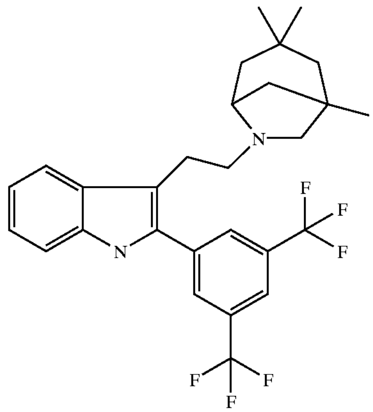 | 508.56 | 510 |
| 164 | 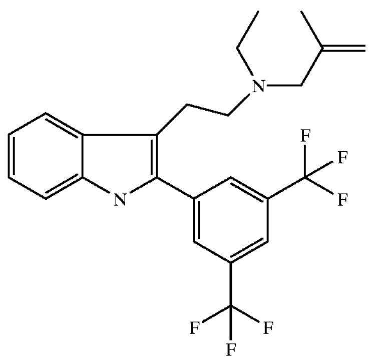 | 454.46 | 455 |
| 165 | 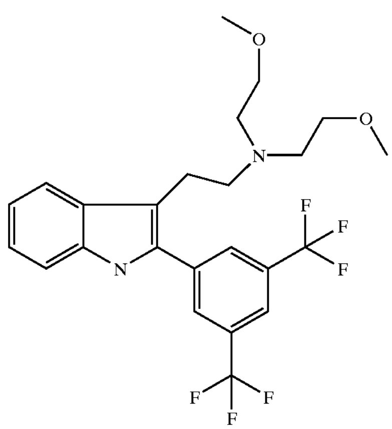 | 488.48 | 489 |

-continued
| Example | Structure | mol weight | m/z (M + 1) + |
|---------|-----------|------------|----------------|
| 166 | 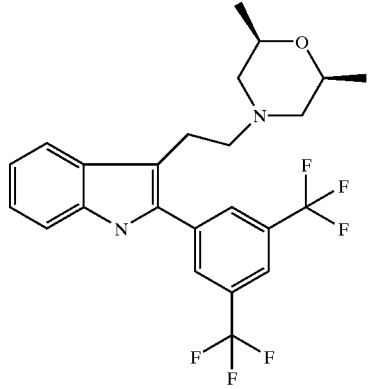 | 470.46 | 471 |
| 167 | 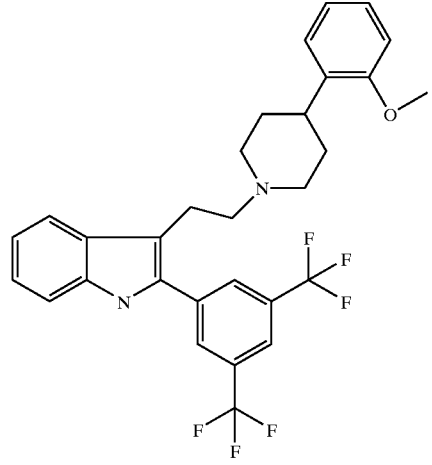 | 546.56 | 548 |
| 168 | 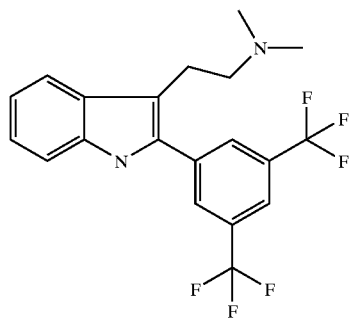 | 400.37 | 401 |

-continued
| Example | Structure | mol weight | m/z (M + 1) + |
|---|---|---|---|
| 169 | 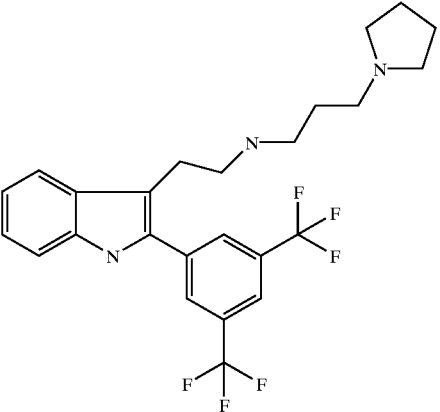 | 483.50 | 485 |
| 170 | 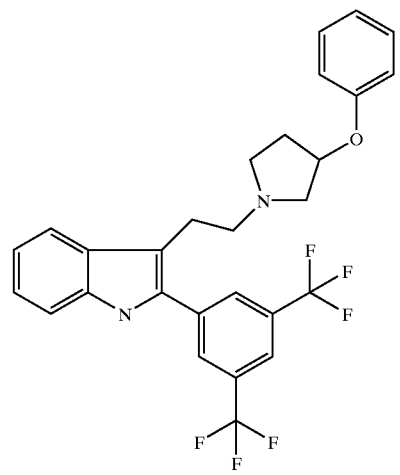 | 518.51 | 520 |
| 171 | 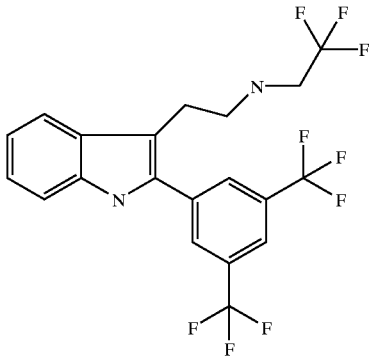 | 454.34 | 455 |
| 172 | 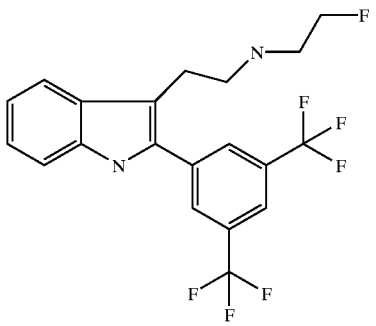 | 418.36 | 419 |

-continued
| Example | Structure | mol weight | m/z (M + 1) + |
|---|---|---|---|
| 173 | 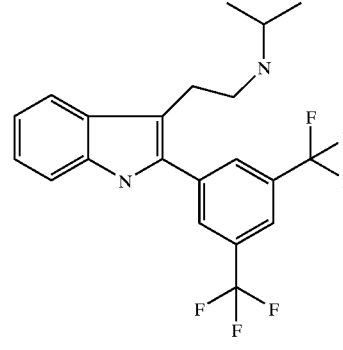 | 414.40 | 415 |
| 174 | 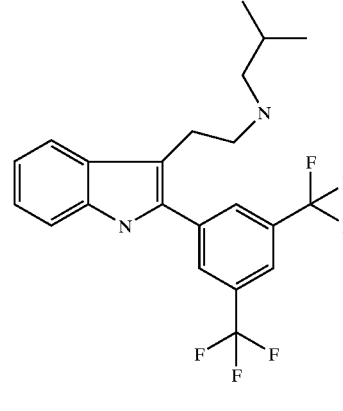 | 428.42 | 429 |
| 175 | 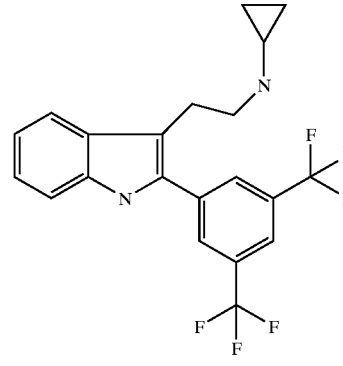 | 412.38 | 413 |
| 176 | 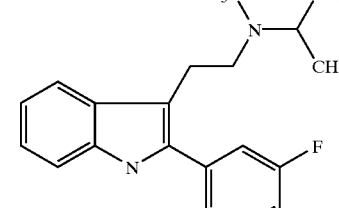 | 310.42 | 311 |

-continued

| Example | Structure | mol weight | m/z (M + 1) + |
|---|---|---|---|
| 177 | 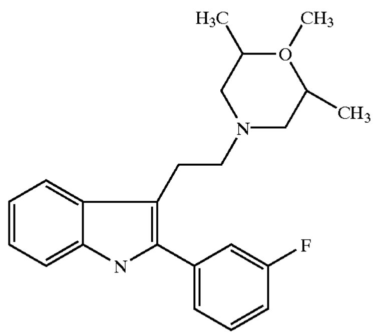 | 366.53 | 368 |
| 178 | 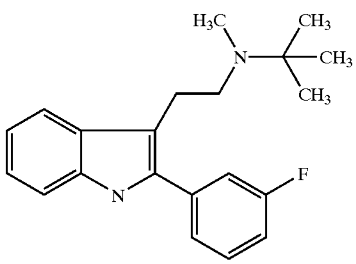 | 324.45 | 325 |
| 179 | 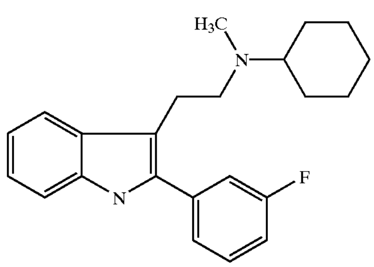 | 350.48 | 351 |
| 180 | 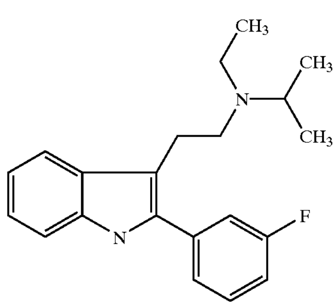 | 324.45 | 325 |
| 181 | 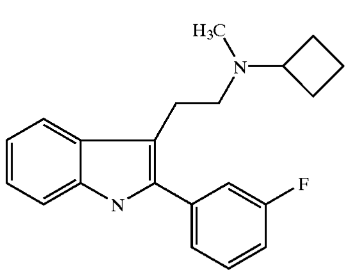 | 322.43 | 323 |

-continued

| Example | Structure | mol weight | m/z (M + 1) + |
|---|---|---|---|
| 182 | (thiomorpholine-N-ethyl)-2-(3-fluorophenyl)-1H-indole | 340.47 | 341 |
| 183 | 3-(2-(N,N-dipentylamino)ethyl)-2-(3-fluorophenyl)-1H-indole | 394.58 | 396 |
| 184 | 3-(2-(N-methyl-N-propylamino)ethyl)-2-(3-fluorophenyl)-1H-indole | 310.42 | 311 |
| 185 | 3-(2-(N,N-dipropylamino)ethyl)-2-(3-fluorophenyl)-1H-indole | 338.47 | 339 |
| 186 | 3-(2-(azepan-1-yl)ethyl)-2-(3-fluorophenyl)-1H-indole | 336.46 | 337 |

-continued

| Example | Structure | mol weight | m/z (M + 1) + |
|---|---|---|---|
| 187 | 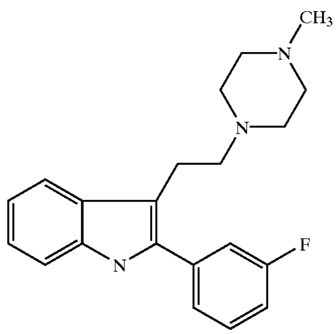 | 337.44 | 338 |
| 188 | 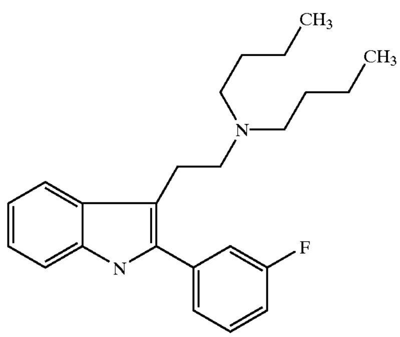 | 366.53 | 368 |
| 189 | 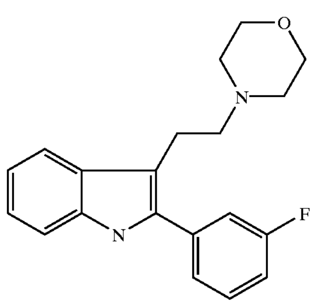 | 324.40 | 325 |
| 190 | 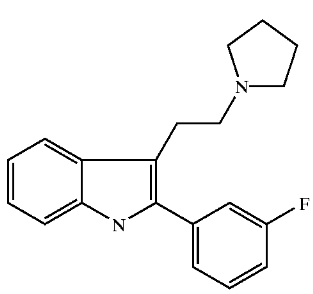 | 308.40 | 309 |

-continued
| Example | Structure | mol weight | m/z (M + 1) + |
|---|---|---|---|
| 191 | 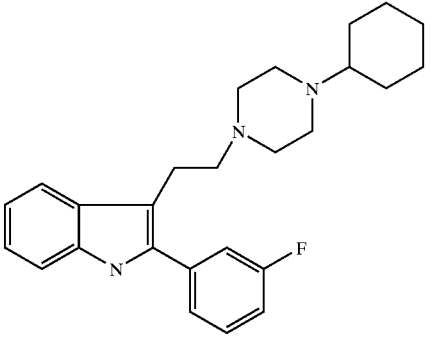 | 405.56 | 407 |
| 192 | 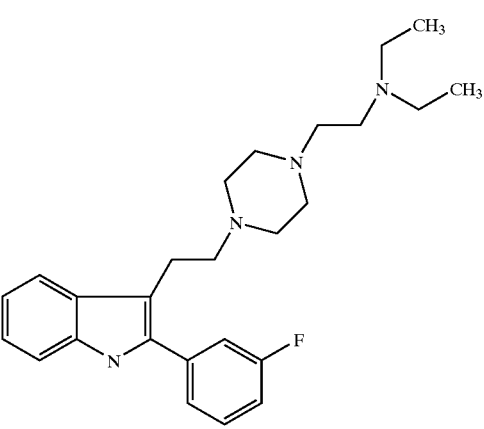 | 422.59 | 424 |
| 193 | 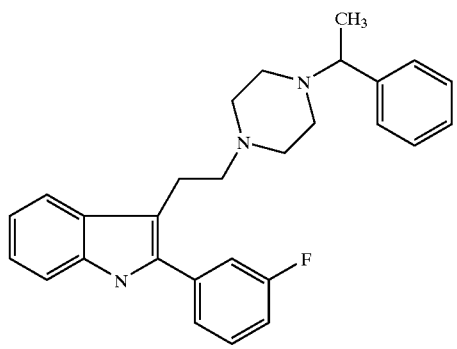 | 427.57 | 429 |
| 194 | 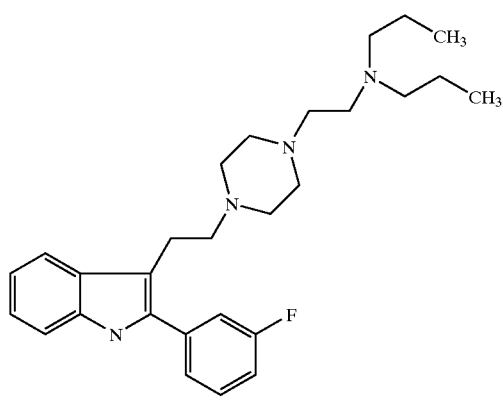 | 450.65 | 452 |

-continued

| Example | Structure | mol weight | m/z (M + 1)+ |
|---------|-----------|------------|--------------|
| 195 | 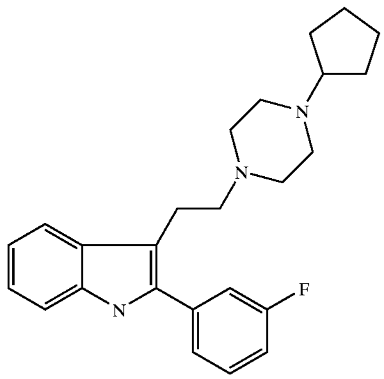 | 391.54 | 393 |
| 196 | 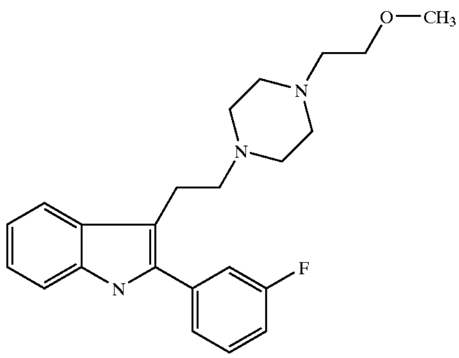 | 381.50 | 382 |
| 197 | 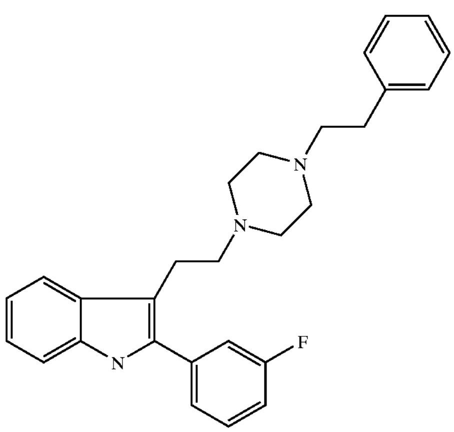 | 427.57 | 429 |
| 198 | 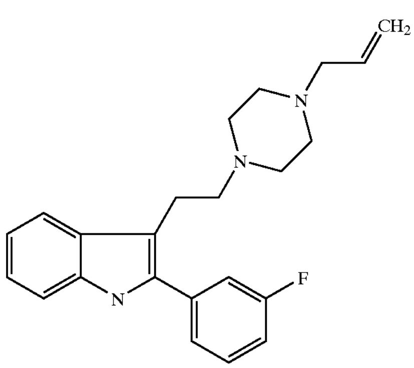 | 363.48 | 364 |

-continued
| Example | Structure | mol weight | m/z (M + 1) + |
|---|---|---|---|
| 199 | 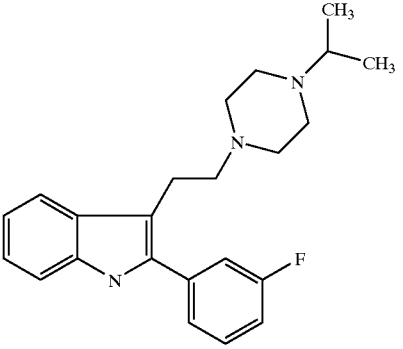 | 365.50 | 366 |
| 200 | 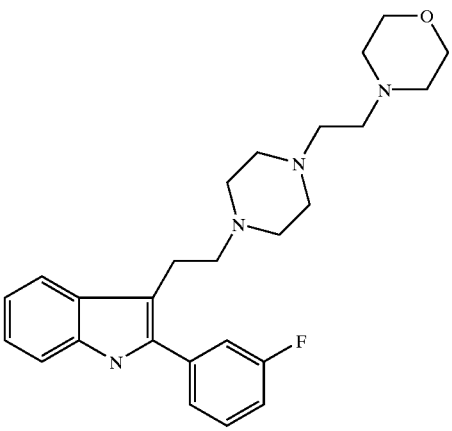 | 436.58 | 438 |
| 201 | 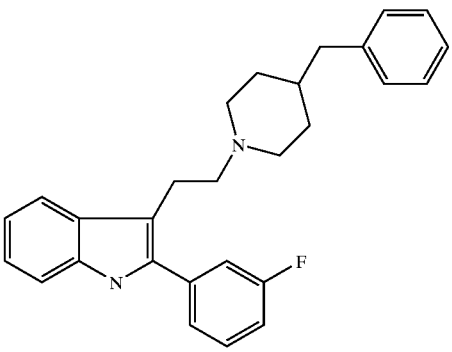 | 412.56 | 414 |
| 202 | 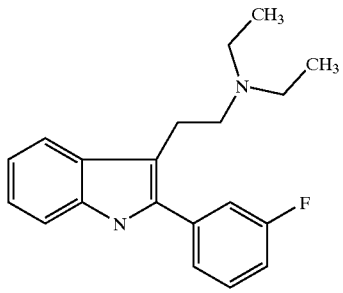 | 310.42 | 311 |

-continued

| Example | Structure | mol weight | m/z (M + 1) + |
|---|---|---|---|
| 203 | 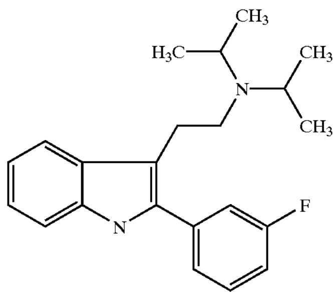 | 338.47 | 339 |
| 204 | 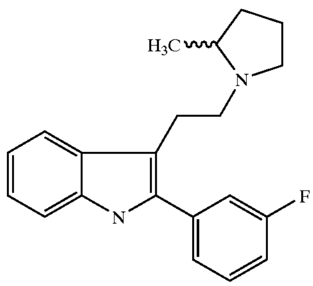 | 322.43 | 323 |
| 205 | 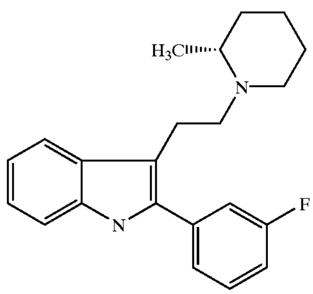 | 336.46 | 337 |
| 206 | 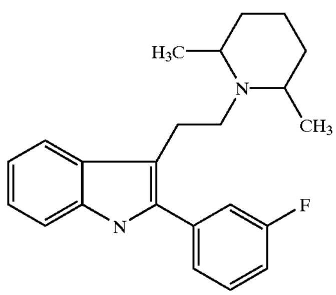 | 350.48 | 351 |
| 207 | 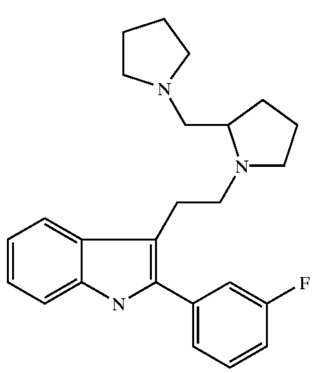 | 391.54 | 393 |

-continued
| Example | Structure | mol weight | m/z (M + 1) + |
|---|---|---|---|
| 208 | 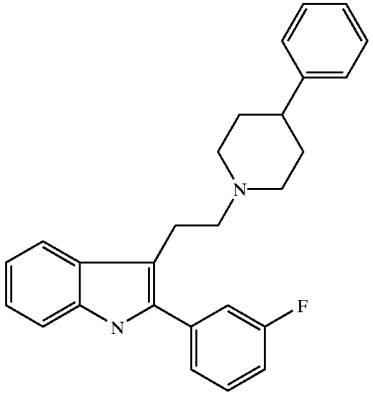 | 398.53 | 400 |
| 209 | 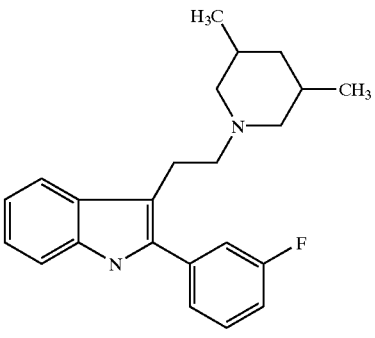 | 350.48 | 351 |
| 210 | 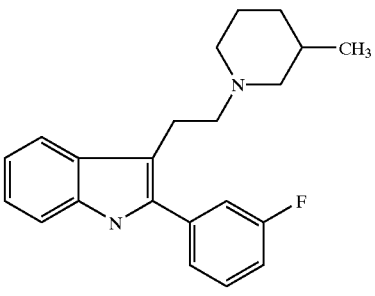 | 336.46 | 337 |
| 211 | 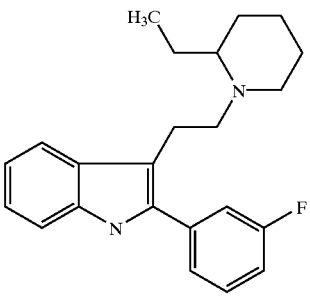 | 350.48 | 351 |

-continued

| Example | Structure | mol weight | m/z (M + 1) + |
|---|---|---|---|
| 212 | 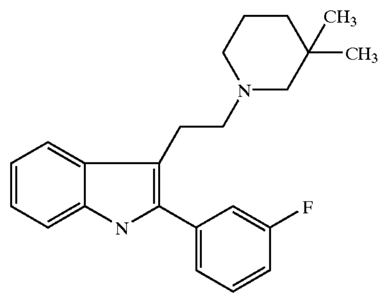 | 350.48 | 351 |
| 213 | 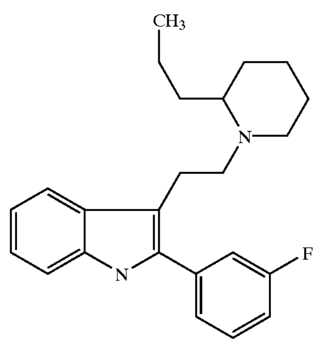 | 364.51 | 366 |
| 214 | 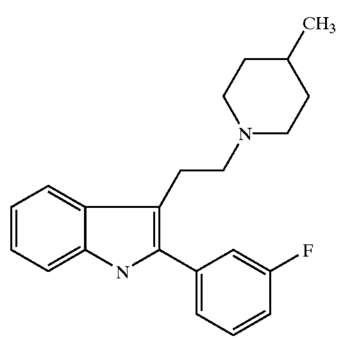 | 336.46 | 337 |
| 215 | 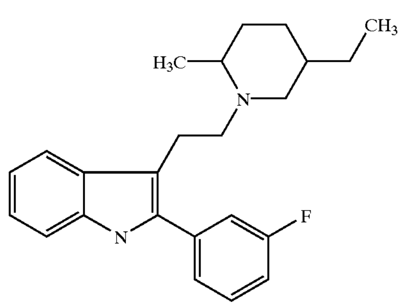 | 364.51 | 366 |

-continued
| Example | Structure | mol weight | m/z (M + 1) + |
|---|---|---|---|
| 216 | 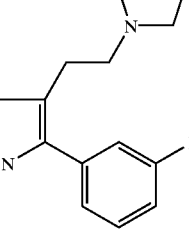 | 352.46 | 353 |
| 217 | 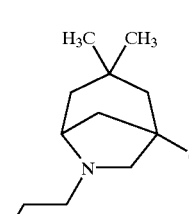 | 390.55 | 392 |
| 218 | 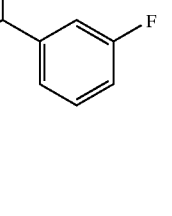 | 336.46 | 337 |
| 219 | 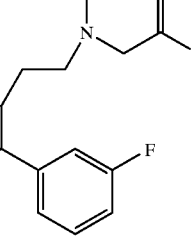 | 392.56 | 394 |

-continued
| Example | Structure | mol weight | m/z (M + 1) + |
|---|---|---|---|
| 220 | 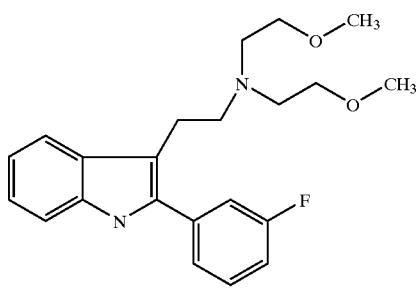 | 370.47 | 371 |
| 221 | 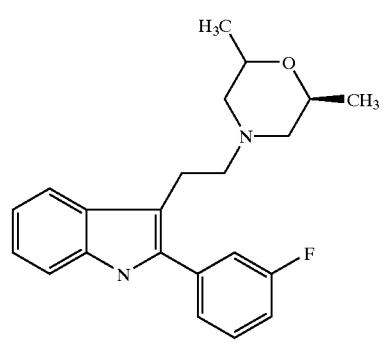 | 352.46 | 353 |
| 222 | 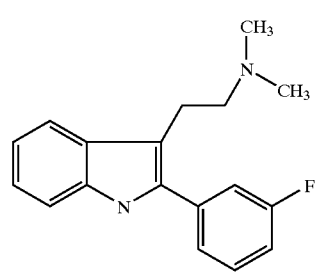 | 282.36 | 283 |
| 223 | 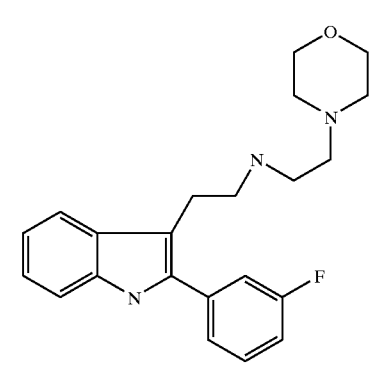 | 367.47 | 368 |

-continued
| Example | Structure | mol weight | m/z (M + 1) + |
|---|---|---|---|
| 224 | 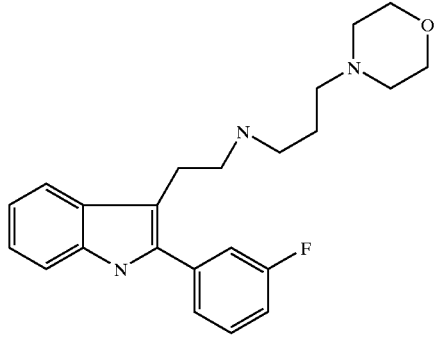 | 381.50 | 382 |
| 225 | 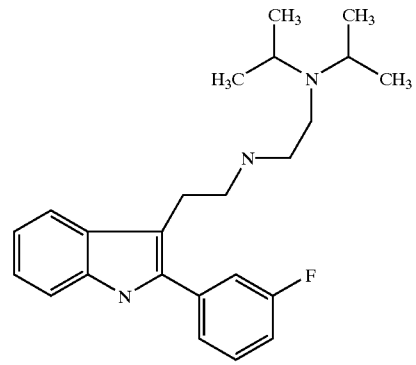 | 381.54 | 383 |
| 226 | 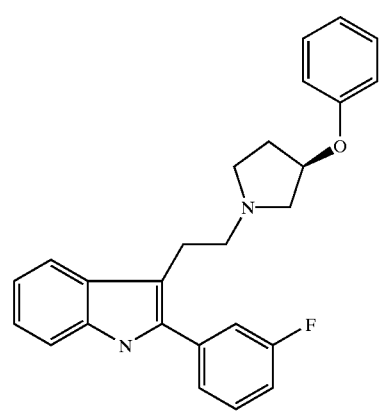 | 400.50 | 402 |
| 227 | 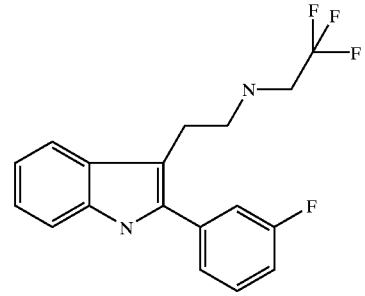 | 336.34 | 337 |

-continued

| Example | Structure | mol weight | m/z (M + 1) + |
|---|---|---|---|
| 228 | 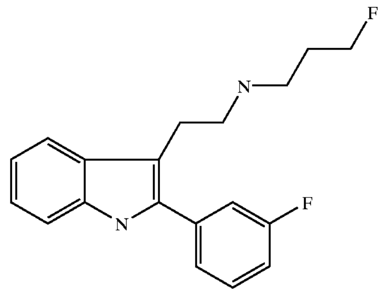 | 314.38 | 315 |
| 229 | 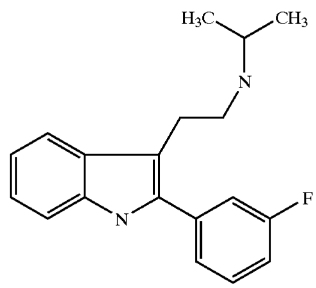 | 296.39 | 297 |
| 230 | 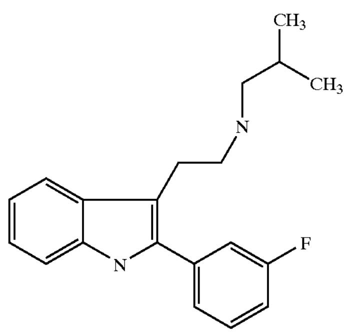 | 310.42 | 311 |
| 231 | 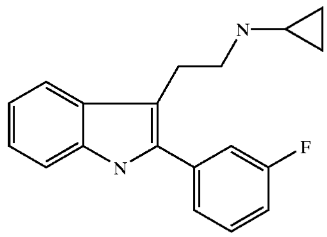 | 294.38 | 295 |

What is claimed is:

1. A compound having formula I, or a pharmaceutically acceptable salt thereof;

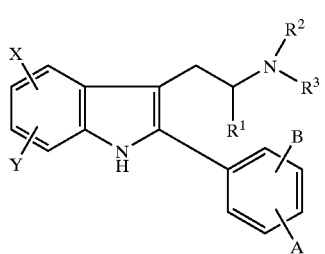

(I)

wherein

A represents hydrogen, halogen, cyano, nitro, trifluoromethyl, trifluoromethoxy, $C_{1-6}$ alkyl or $C_{1-6}$ alkoxy;

B represents trifluoromethyl or trifluoromethoxy,:

X and Y independently represent hydrogen, halogen, $C_{1-6}$ alkyl, $C_{1-6}$ alkoxy or phenyl;

$R^1$ represents hydrogen or $C_{1-6}$ alkyl;

$R^2$ represents hydrogen, methyl, ethyl, 2-methoxyethyl, n-propyl, isopropyl, n-butyl, 2-methylpropyl, tert-butyl or n-pentyl; and $R^3$ represents $C_{1-6}$ alkyl, $C_{2-6}$ alkenyl, $C_{3-9}$ cycloalkyl, aryl, $C_{3-7}$ heterocycloalkyl, $C_{3-7}$ heterocycloalkyl($C_{1-6}$) alkyl, heteroaryl or heteroaryl($C_{1-6}$)alkyl, any of which groups may be optionally substituted by one or more substituents; or $R^2$ and $R^3$ taken together with the intervening nitrogen atom represent a group of formula (a), (b), (c), (d), (e), (f), (g), (h), (i), (j), (k), (l) or (m):

(a) 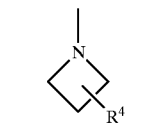

(b) 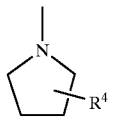

(c) 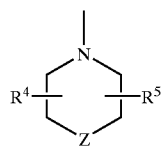

(d) 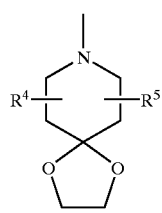

(e) 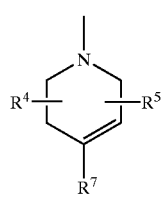

(f) 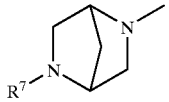

(g) 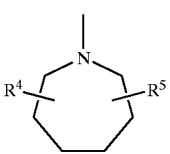

(h) 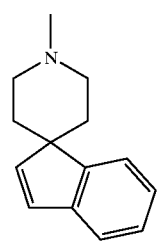

(i) 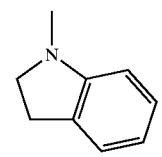

(j) 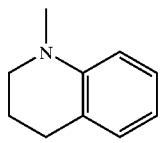

(k) 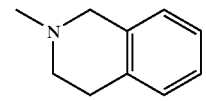

(l) 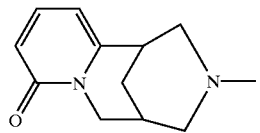

(m) 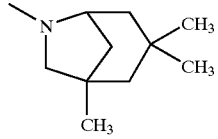

in which the broken line represents an optional chemical bond;

Z represents oxygen, sulphur, N—$R^6$ or $CR^7R^8$;

$R^4$ represents hydrogen, $C_{1-6}$ alkyl, $C_{1-6}$ alkoxy($C_{1-6}$)alkyl, $C_{3-7}$ heterocycloalkyl($C_{1-6}$)alkyl or aryloxy;

$R^5$ represents hydrogen, $C_{1-6}$ alkyl or $C_{1-6}$ alkoxy($C_{1-6}$)alkyl;

$R^6$ represents hydrogen, —$COR^9$ or —$CO_2R^9$; or $C_{1-6}$ alkyl, $C_{2-6}$ alkenyl, $C_{3-9}$ cycloalkyl, aryl($C_{1-6}$)alkyl, aryl($C_{2-6}$)alkenyl, $C_{3-7}$ heterocycloalkyl($C_{1-6}$)alkyl or heteroaryl, any of which groups may be optionally substituted by one or more substituents;

$R^7$ represents hydrogen, hydrocarbon, a heterocyclic group, —$COR^9$ or —$CO_2R^9$, $R^8$ represents hydrogen, phenyl or acetoxy; and $R^9$ represents $C_{1-6}$ alkyl.

2. A compound of formula IA, or a pharmaceutically acceptable salt thereof:

(IA) 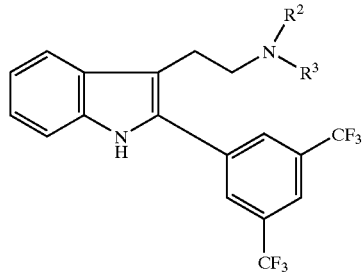

wherein $R^2$ and $R^3$ are as defined in claim 1.

3. A compound having formula I, or a pharmaceutically acceptable salt thereof:

(I)

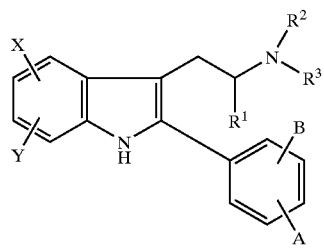

wherein

- A and B independently represent hydrogen, halogen, cyano, nitro, trifluoromethyl, trifluoromethoxy, $C_{1-6}$ alkyl or $C_{1-6}$ alkoxy;
- X represents hydrogen, halogen, $C_{1-6}$ alkyl, $C_{1-6}$ alkoxy or phenyl;
- Y represents phenyl;
- $R^1$ represents hydrogen or $C_{1-6}$ alkyl;
- $R^2$ represents hydrogen, methyl, ethyl, 2-methoxyethyl, n-propyl, isopropyl, n-butyl, 2-methylpropyl, tert-butyl or n-pentyl; and
- $R^3$ represents $C_{1-6}$ alkyl, $C_{2-6}$ alkenyl, $C_{3-9}$ cycloalkyl, aryl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or
- $R^2$ and $R^3$ taken together with the intervening nitrogen atom represent a group of formula (a), (b), (c), (d), (e), (f), (g), (h), (i), (j), (k), (l) or (m):

(a)
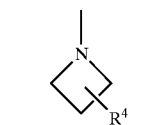

(b)
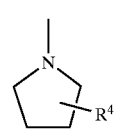

(c)
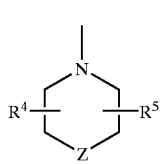

(d)
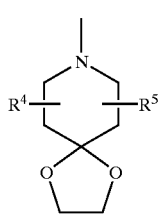

(e)
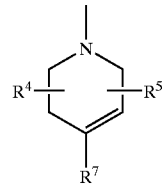

(f)
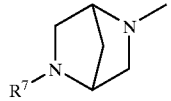

(g)
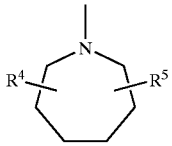

(h)
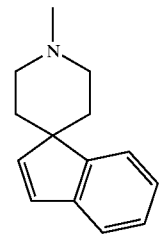

(i)
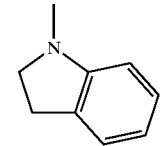

(j)
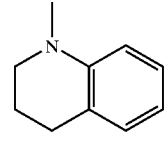

(k)
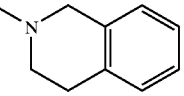

(l)
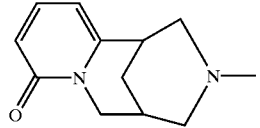

(m)
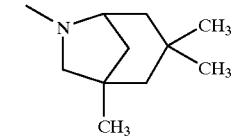

in which the broken line represents an optional chemical bond;

- Z represents oxygen, sulphur, N—$R^6$ or $CR^7R^8$;
- $R^4$ represents hydrogen, $C_{1-6}$ alkyl, $C_{1-6}$ alkoxy($C_{1-6}$) alkyl, $C_{3-7}$ heterocycloalkyl($C_{1-6}$)alkyl or aryloxy;
- $R^5$ represents hydrogen, $C_{1-6}$ alkyl or $C_{1-6}$ alkoxy($C_{1-6}$) alkyl;

$R^6$ represents hydrogen, —COR$^9$ or —CO$_2$R$^9$; or C$_{1-6}$ alkyl, C$_{2-6}$ alkenyl, C$_{3-9}$ cycloalkyl, aryl(C$_{1-6}$)alkyl, aryl(C$_{2-6}$)alkenyl, C$_{3-7}$ heterocycloalkyl(C$_{1-6}$)alkyl or heteroaryl, any of which groups may be optionally substituted by one or more substituents;

$R^7$ represents hydrogen, hydrocarbon, a heterocyclic group, —COR$^9$ or —CO$_2$R$^9$;

$R^8$ represents hydrogen, phenyl or acetoxy; and $R^9$ represents C$_{1-6}$ alkyl.

4. A pharmaceutical composition comprising a therapeutically effective amount of a compound as claimed in claim 1 in association with a pharmaceutically acceptable carrier.

5. A pharmaceutical composition comprising a therapeutically effective amount of a compound as claimed in claim 2 in association with a pharmaceutically acceptable carrier.

6. A pharmaceutical composition comprising a therapeutically effective amount of a compound as claimed in claim 3 in association with a pharmaceutically acceptable carrier.

7. A pharmaceutical composition comprising a therapeutically effective amount of a compound having formula I, or a pharmaceutically acceptable salt thereof, in association with a pharmaceutically acceptable carrier, further comprising a second anti-schizophrenic medicament, or a pharmaceutically acceptable salt thereof:

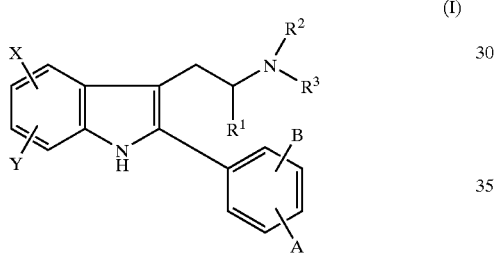

(I)

wherein

A and B independently represent hydrogen, halogen, cyano, nitro, trifluoromethyl, trifluoromethoxy, C$_{1-6}$ alkyl or C$_{1-6}$ alkoxy;

X and Y independently represent hydrogen, halogen, C$_{1-6}$ alkyl, C$_{1-6}$ alkoxy or phenyl;

$R^1$ represents hydrogen or C$_{1-6}$ alkyl;

$R^2$ represents hydrogen, methyl, ethyl, 2-methoxyethyl, n-propyl, isopropyl, n-butyl, 2-methylpropyl, tert-butyl or n-pentyl; and $R^3$ represents C$_{1-6}$ alkyl, C$_{2-6}$ alkenyl, C$_{3-9}$ cycloalkyl, aryl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents, with the proviso that the heterocycloalkyl(C$_{1-6}$)alkyl and heteroaryl(C$_{1-6}$)alkyl groups do not include the heterocycle and heteroaryl groups selected from pyridine N-oxide, pyridine, 2-hydroxypyridine, indole, benzimidazole, quinoline, pyrimidine, imidazole, naphthyridine, and tetrahydronaphthyridine; or $R^2$ and $R^3$ taken together with the intervening nitrogen atom represent a group of formula (a), (b), (c), (d), (e), (f), (g), (h), (i), G), (k), (l) or (m):

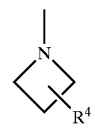

(a)

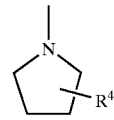

(b)

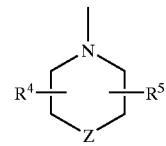

(c)

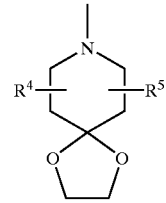

(d)

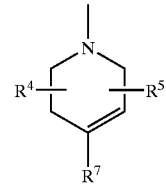

(e)

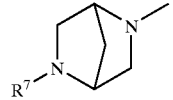

(f)

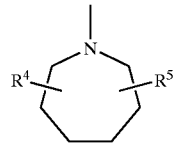

(g)

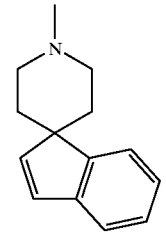

(h)

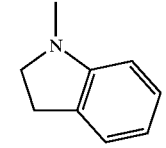

(i)

-continued

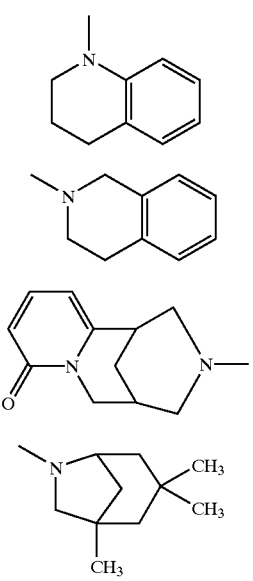

in which the broken line represents an optional chemical bond;

Z represents oxygen, sulphur, N—$R^6$ or $CR^7R^8$;

$R_4$ represents hydrogen, $C_{1-6}$ alkyl, $C_{1-6}$ alkoxy($C_{1-6}$) alkyl, $C_{3-7}$ heterocycloalkyl($C_{1-6}$)alkyl or aryloxy, $R^5$ represents hydrogen, $C_{1-6}$ alkyl or $C_{1-6}$ alkoxy($C_{1-6}$) alkyl;

$R^6$ represents hydrogen, —$COR^9$ or —$CO_2R^9$; or $C_{1-6}$ alkyl, $C_{2-6}$ alkenyl, $C_{3-9}$ cycloalkyl, aryl($C_{1-6}$)alkyl, aryl($C_{2-6}$)alkenyl, $C_{3-7}$ heterocycloalkyl]($C_{1-6}$)alkyl or heteroaryl, any of which groups may be optionally substituted by one or more substituents;

$R^7$ represents hydrogen, hydrocarbon, a heterocyclic group, —$COR^9$ or —$CO_2R^9$;

$R^8$ represents hydrogen, phenyl or acetoxy; and $R^9$ represents $C_{1-6}$ alkyl; with the proviso that:
(i) when A and B independently represent hydrogen, halogen, cyano, nitro, alkyl or alkoxy, and X and Y independently represent hydrogen, halogen, alkyl or alkoxy, then $R^3$ does not represent alkyl, and $R^2$ and $R^3$ taken together with the intervening nitrogen atom do not represent piperidin-1-yl or morpholin-4-yl; and
(ii) when A, B, X, Y and $R^1$ each represents hydrogen, then $R^2$ and $R^3$ taken together with the intervening nitrogen atom do not represent piperidin-1-yl, morpholin-4-yl, pyrrolidin-1-yl, 2-methylpiperidin-1-yl or homopiperidin-1-yl.

8. A pharmaceutical composition as claimed in claim 4, further comprising a second anti-schizophrenic medicament.

9. A composition as claimed in claim 5 further comprising a second anti-schizophrenic medicament.

10. A composition as claimed in claim 6 further comprising a second anti-schizophrenic medicament.

11. A method for the treatment of clinical conditions for which a selective antagonist of 5-$HT_{2A}$ receptors is indicated which comprises administering to a patient in need of such treatment an effective amount of a compound having formula I, or a pharmaceutically acceptable salt thereof:

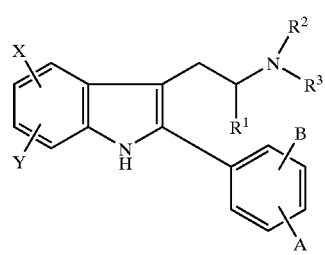

wherein

A and B independently represent hydrogen, halogen, cyano, nitro, trifluoromethyl, trifluoromethoxy, $C_{1-6}$ alkyl or $C_{1-6}$ alkoxy;

X and Y independently represent hydrogen, halogen, $C_{1-6}$ alkyl, $C_{1-6}$ alkoxy or phenyl;

$R^1$ represents hydrogen or $C_{1-6}$ alkyl;

$R^2$ represents hydrogen, methyl, ethyl, 2-methoxyethyl, n-propyl, isopropyl, n-butyl, 2-methylpropyl, tert-butyl or n-pentyl; and $R^3$ represents $C_{1-6}$ alkyl, $C_{2-6}$ alkenyl, $C_{3-9}$ cycloalkyl, aryl, $C_{3-7}$ heterocycloalkyl, $C_{3-7}$ heterocycloalkyl($C_{1-6}$) alkyl, heteroaryl or heteroaryl($C_{1-6}$)alkyl, any of which groups may be optionally substituted by one or more substituents, with the proviso that the heterocycloalkyl ($C_{1-6}$)alkyl and heteroaryl($C_{1-6}$)alkyl groups do not include the heterocycle and heteroaryl groups selected from pyridine N-oxide, pyridine, 2-hydroxypyridine, indole, benzimidazole, quinoline, pyrimidine, imidazole, naphthyridine, and tetrahydronaphthyridine; or $R^2$ and $R^3$ taken together with the intervening nitrogen atom represent a group of formula (a), (b), (c), (d), (e), (f), (g), (h), (i), (j), (k), (l) or (m):

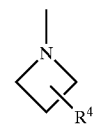

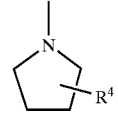

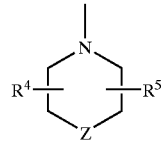

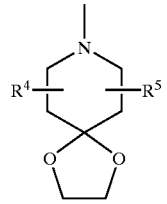

-continued (e) 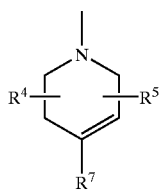

(f) 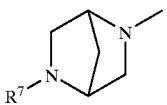

(g) 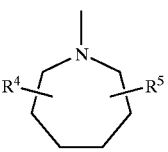

(h) 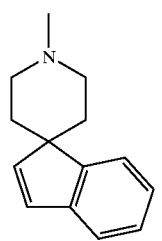

(i) 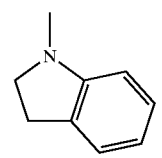

(j) 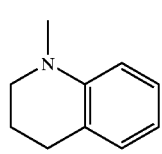

(k) 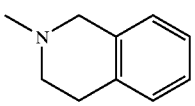

(l) 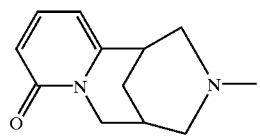

-continued (m) 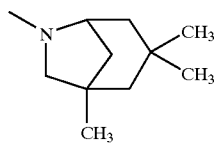

in which the broken line represents an optional chemical bond;

Z represents oxygen, sulphur, N—$R^6$ or $CR^7R^8$;

$R^4$ represents hydrogen, $C_{1-6}$ alkyl, $C^{1-6}$ alkoxy($C^{1-6}$) alkyl, $C_{3-7}$ heterocycloalkyl($C_{1-6}$)alkyl or aryloxy;

$R^5$ represents hydrogen, $C_{1-6}$ alkyl or $C_{1-6}$ alkoxy($C_{1-6}$) alkyl;

$R^6$ represents hydrogen, —$COR^9$ or —$CO_2R^9$; or $C_{1-6}$ alkyl, $C_{2-6}$ alkenyl, $C_{3-9}$ cycloalkyl, aryl($C_{1-6}$)alkyl, aryl($C_{2-6}$)alkenyl, $C_{3-7}$ heterocycloalkyl($C_{1-6}$)alkyl or heteroaryl, any of which groups may be optionally substituted by one or more substituents;

$R^7$ represents hydrogen, hydrocarbon, a heterocyclic group, —$COR^9$ or —$CO_2R^9$;

$R^8$ represents hydrogen, phenyl or acetoxy; and $R^9$ represents $C_{1-6}$ alkyl; with the proviso that:

(i) when A and B independently represent hydrogen, halogen, cyano, nitro, alkyl or alkoxy, and X and Y independently represent hydrogen, halogen, alkyl or alkoxy, than $R^3$ does not represent alkyl, and $R^2$ and $R^3$ taken together with the intervening nitrogen atom do not represent piperidin-1-yl or morpholin-4yl; and (ii) when A, B, X, Y and $R^1$ each represents hydrogen, then $R^2$ and $R^3$ taken together with the intervening nitrogen atom do not represent piperidin-1-yl, morpholin-4-yl, pyrrolidin-1-yl, 2-methylpiperidin-1-yl or homopiperidin-1-yl.

12. A method for the treatment of clinical conditions for which a selective antagonist of 5-$HT_{2A}$ receptors is indicated, which comprises administering to a patient in need of such treatment an effective amount of a compound as claimed in claim 1.

13. A method for the treatment of clinical conditions for which a selective antagonist of $^5$-$HT_{2A}$ receptors is indicated, which comprises administering to a patient in need of such treatment an effective amount of a compound as claimed in claim 2.

14. A method for the treatment of clinical conditions for which a selective antagonist of $^5$-$HT_{2A}$ receptors is indicated, which comprises administering to a patient in need of such treatment an effective amount of a compound as claimed in claim 3.

* * * * *